(12) United States Patent
Waycullis et al.

(10) Patent No.: US 8,802,908 B2
(45) Date of Patent: *Aug. 12, 2014

(54) PROCESSES AND SYSTEMS FOR SEPARATE, PARALLEL METHANE AND HIGHER ALKANES' BROMINATION

(71) Applicant: Marathon GTF Technology, LTD., Houston, TX (US)

(72) Inventors: John J. Waycullis, Cypress, TX (US); Sagar B. Gadewar, Goleta, CA (US); Raphael Thomas, Houston, TX (US)

(73) Assignee: Marathon GTF Technology, Ltd., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/647,002

(22) Filed: Oct. 8, 2012

(65) Prior Publication Data

US 2013/0102821 A1 Apr. 25, 2013

Related U.S. Application Data

(60) Provisional application No. 61/550,059, filed on Oct. 21, 2011.

(51) Int. Cl.
*C07C 1/00* (2006.01)
*C07C 2/00* (2006.01)

(52) U.S. Cl.
USPC ........... 585/359; 585/943; 585/408; 585/310; 585/469; 585/462; 585/733; 585/422

(58) Field of Classification Search
None
See application file for complete search history.

(56) References Cited

U.S. PATENT DOCUMENTS

| | | |
|---|---|---|
| 2,168,260 A | 8/1939 | Heisel et al. |
| 2,246,082 A | 6/1941 | Vaughan et al. |
| 2,320,257 A | 5/1943 | Beekhuis |

(Continued)

FOREIGN PATENT DOCUMENTS

| | | |
|---|---|---|
| CA | 1099656 | 4/1981 |
| CA | 1101441 | 5/1981 |

(Continued)

OTHER PUBLICATIONS

Henshuiinkai, Kagaku Daijiten; Kagaku Daijiten 4, Japan, Kyoritsu Publisher, Oct. 15, 1963; pp. 652-654.

(Continued)

*Primary Examiner* — Tam M Nguyen
(74) *Attorney, Agent, or Firm* — Jack E. Ebel; Corey S. Tumey; Rodney F. Brown

(57) ABSTRACT

Process and systems for alkane bromination and, in one or more embodiments, to separate, parallel methane and higher alkanes bromination in a bromine-based process. An embodiment discloses a bromine-based process for converting alkanes to liquid hydrocarbons that includes alkanes bromination, the process comprising: brominating a methane stream comprising methane and having less than about 2 mol % of ethane to form methane bromination products comprising brominated methane and a first fraction of hydrogen bromide; separately brominating a C2+ alkane stream comprising an alkane having 2 or more carbon atoms to form C2+ methane bromination products comprising brominated alkanes having 2 or more carbon atoms and a second fraction of hydrogen bromide; and catalytically reacting at least a portion of the brominated methane and the brominated alkanes to form higher molecular hydrocarbons.

20 Claims, 10 Drawing Sheets

(56) References Cited

U.S. PATENT DOCUMENTS

| | | |
|---|---|---|
| 2,488,083 A | 11/1949 | Gorin et al. |
| 2,536,457 A | 1/1951 | Mugdan |
| 2,666,024 A | 1/1954 | Low et al. |
| 2,677,598 A | 5/1954 | Crummett et al. |
| 2,809,930 A | 10/1957 | Miller |
| 2,941,014 A | 6/1960 | Rothweiler et al. |
| 3,076,784 A | 2/1963 | Schulte-Huemann et al. |
| 3,172,915 A | 3/1965 | Borkowski et al. |
| 3,181,934 A | 5/1965 | Davis |
| 3,233,972 A | 2/1966 | Walker et al. |
| 3,246,043 A | 4/1966 | Rosset et al. |
| 3,254,023 A | 5/1966 | Miale et al. |
| 3,273,964 A | 9/1966 | Rosset |
| 3,291,708 A | 12/1966 | Juda |
| 3,294,846 A | 12/1966 | Livak et al. |
| 3,310,380 A | 3/1967 | Lester |
| 3,314,762 A | 4/1967 | Hahn |
| 3,346,340 A | 10/1967 | Louvar et al. |
| 3,353,916 A | 11/1967 | Lester |
| 3,353,919 A | 11/1967 | Stockman |
| 3,379,506 A | 4/1968 | Massonne et al. |
| 3,468,968 A | 9/1969 | Baker et al. |
| 3,496,242 A | 2/1970 | Berkowitz et al. |
| 3,562,321 A | 2/1971 | Borkowski et al. |
| 3,598,876 A | 8/1971 | Bloch |
| 3,615,265 A | 10/1971 | Gartner |
| 3,642,447 A | 2/1972 | Hahn et al. |
| 3,657,367 A | 4/1972 | Blake et al. |
| 3,670,037 A | 6/1972 | Dugan |
| 3,673,264 A | 6/1972 | Kuhn |
| 3,679,758 A | 7/1972 | Schneider |
| 3,702,886 A | 11/1972 | Argauer et al. |
| 3,705,196 A | 12/1972 | Turner |
| 3,799,997 A | 3/1974 | Schmerling |
| 3,816,599 A | 6/1974 | Kafes |
| 3,865,886 A | 2/1975 | Schindler et al. |
| 3,876,715 A | 4/1975 | McNulty et al. |
| 3,879,473 A | 4/1975 | Stapp |
| 3,879,480 A | 4/1975 | Riegel et al. |
| 3,883,651 A | 5/1975 | Woitun et al. |
| 3,886,287 A | 5/1975 | Kobayashi et al. |
| 3,894,103 A | 7/1975 | Chang et al. |
| 3,894,104 A | 7/1975 | Chang et al. |
| 3,894,105 A | 7/1975 | Chang et al. |
| 3,894,107 A | 7/1975 | Butter et al. |
| 3,907,917 A | 9/1975 | Forth |
| 3,919,336 A | 11/1975 | Kurtz |
| 3,920,764 A | 11/1975 | Riegel et al. |
| 3,923,913 A | 12/1975 | Antonini et al. |
| 3,927,111 A | 12/1975 | Robinson |
| 3,928,483 A | 12/1975 | Chang et al. |
| 3,959,450 A | 5/1976 | Calloue et al. |
| 3,965,205 A | 6/1976 | Garwood et al. |
| 3,974,062 A | 8/1976 | Owen et al. |
| 3,987,119 A | 10/1976 | Kurtz et al. |
| 3,992,466 A | 11/1976 | Plank et al. |
| 4,006,169 A | 2/1977 | Anderson et al. |
| 4,011,278 A | 3/1977 | Plank et al. |
| 4,025,571 A | 5/1977 | Lago |
| 4,025,572 A | 5/1977 | Lago |
| 4,025,575 A | 5/1977 | Chang et al. |
| 4,025,576 A | 5/1977 | Chang et al. |
| 4,035,285 A | 7/1977 | Owen et al. |
| 4,035,430 A | 7/1977 | Dwyer et al. |
| 4,039,600 A | 8/1977 | Chang |
| 4,044,061 A | 8/1977 | Chang et al. |
| 4,046,819 A | 9/1977 | Schmerling |
| 4,046,825 A | 9/1977 | Owen et al. |
| 4,049,734 A | 9/1977 | Garwood et al. |
| 4,052,471 A | 10/1977 | Pearsall |
| 4,052,472 A | 10/1977 | Given et al. |
| 4,058,576 A | 11/1977 | Chang et al. |
| 4,060,568 A | 11/1977 | Rodewald |
| 4,071,753 A | 1/1978 | Fulenwider et al. |
| 4,072,733 A | 2/1978 | Hargis et al. |
| 4,087,475 A | 5/1978 | Jordan |
| 4,088,706 A | 5/1978 | Kaeding |
| 4,092,368 A | 5/1978 | Smith |
| 4,105,755 A | 8/1978 | Darnell et al. |
| 4,110,180 A | 8/1978 | Nidola et al. |
| 4,117,251 A | 9/1978 | Kaufhold et al. |
| 4,129,604 A | 12/1978 | Tsao |
| 4,133,838 A | 1/1979 | Pearson |
| 4,133,966 A | 1/1979 | Pretzer et al. |
| 4,138,440 A | 2/1979 | Chang et al. |
| 4,143,084 A | 3/1979 | Kaeding et al. |
| 4,156,698 A | 5/1979 | Dwyer et al. |
| 4,169,862 A | 10/1979 | Eden |
| 4,172,099 A | 10/1979 | Severino |
| 4,187,255 A | 2/1980 | Dodd |
| 4,191,618 A | 3/1980 | Coker et al. |
| 4,194,990 A | 3/1980 | Pieters et al. |
| 4,197,420 A | 4/1980 | Ferraris et al. |
| 4,219,604 A | 8/1980 | Kakimi et al. |
| 4,219,680 A | 8/1980 | Konig et al. |
| 4,249,031 A | 2/1981 | Drent et al. |
| 4,252,687 A | 2/1981 | Dale et al. |
| 4,270,929 A | 6/1981 | Dang Vu et al. |
| 4,272,338 A | 6/1981 | Lynch et al. |
| 4,282,159 A | 8/1981 | Davidson et al. |
| 4,300,005 A | 11/1981 | Li |
| 4,300,009 A | 11/1981 | Haag et al. |
| 4,301,253 A | 11/1981 | Warren |
| 4,302,619 A | 11/1981 | Gross et al. |
| 4,307,261 A | 12/1981 | Beard, Jr. et al. |
| 4,308,403 A | 12/1981 | Knifton |
| 4,311,865 A | 1/1982 | Chen et al. |
| 4,317,800 A | 3/1982 | Sloterdijk et al. |
| 4,317,934 A | 3/1982 | Seemuth |
| 4,317,943 A | 3/1982 | Knifton |
| 4,320,241 A | 3/1982 | Frankiewicz |
| 4,333,852 A | 6/1982 | Warren |
| 4,347,391 A | 8/1982 | Campbell |
| 4,350,511 A | 9/1982 | Holmes et al. |
| 4,356,159 A | 10/1982 | Norval et al. |
| 4,371,716 A | 2/1983 | Paxson et al. |
| 4,373,109 A | 2/1983 | Olah |
| 4,376,019 A | 3/1983 | Gamlen et al. |
| 4,379,734 A | 4/1983 | Franzen |
| 4,380,682 A | 4/1983 | Leitert et al. |
| 4,384,159 A | 5/1983 | Diesen |
| 4,389,391 A | 6/1983 | Dunn, Jr. |
| 4,410,714 A | 10/1983 | Apanel |
| 4,412,086 A | 10/1983 | Beard, Jr. et al. |
| 4,418,236 A | 11/1983 | Cornelius et al. |
| 4,431,856 A | 2/1984 | Daviduk et al. |
| 4,433,189 A | 2/1984 | Young |
| 4,433,192 A | 2/1984 | Olah |
| 4,439,409 A | 3/1984 | Puppe et al. |
| 4,440,871 A | 4/1984 | Lok et al. |
| 4,443,620 A | 4/1984 | Gelbein et al. |
| 4,462,814 A | 7/1984 | Holmes et al. |
| 4,465,884 A | 8/1984 | Degnan et al. |
| 4,465,893 A | 8/1984 | Olah |
| 4,467,130 A | 8/1984 | Olah |
| 4,467,133 A | 8/1984 | Chang et al. |
| 4,489,210 A | 12/1984 | Judat et al. |
| 4,489,211 A | 12/1984 | Ogura et al. |
| 4,492,657 A | 1/1985 | Heiss |
| 4,496,752 A | 1/1985 | Gelbein et al. |
| 4,497,967 A | 2/1985 | Wan |
| 4,499,314 A | 2/1985 | Seddon et al. |
| 4,506,105 A | 3/1985 | Kaufhold |
| 4,509,955 A | 4/1985 | Hayashi |
| 4,513,092 A | 4/1985 | Chu et al. |
| 4,513,164 A | 4/1985 | Olah |
| 4,523,040 A | 6/1985 | Olah |
| 4,524,227 A | 6/1985 | Fowles et al. |
| 4,524,228 A | 6/1985 | Fowles et al. |
| 4,524,231 A | 6/1985 | Fowles et al. |
| 4,538,014 A | 8/1985 | Miale et al. |
| 4,538,015 A | 8/1985 | Miale et al. |
| 4,540,826 A | 9/1985 | Banasiak et al. |
| 4,543,434 A | 9/1985 | Chang |

(56) References Cited

U.S. PATENT DOCUMENTS

| | | |
|---|---|---|
| 4,544,781 A | 10/1985 | Chao et al. |
| 4,547,612 A | 10/1985 | Tabak |
| 4,550,217 A | 10/1985 | Graziani et al. |
| 4,550,218 A | 10/1985 | Chu |
| 4,568,660 A | 2/1986 | Klosiewicz |
| 4,579,977 A | 4/1986 | Drake |
| 4,579,992 A | 4/1986 | Kaufhold et al. |
| 4,579,996 A | 4/1986 | Font Freide et al. |
| 4,587,375 A | 5/1986 | Debras et al. |
| 4,588,835 A | 5/1986 | Torii et al. |
| 4,590,310 A | 5/1986 | Townsend et al. |
| 4,599,474 A | 7/1986 | Devries et al. |
| 4,605,796 A | 8/1986 | Isogai et al. |
| 4,605,803 A | 8/1986 | Chang et al. |
| 4,621,161 A | 11/1986 | Shihabi |
| 4,621,164 A | 11/1986 | Chang et al. |
| 4,626,607 A | 12/1986 | Jacquinot et al. |
| 4,633,027 A | 12/1986 | Owen et al. |
| 4,634,800 A | 1/1987 | Withers, Jr. et al. |
| 4,642,403 A | 2/1987 | Hyde et al. |
| 4,642,404 A | 2/1987 | Shihabi |
| 4,652,688 A | 3/1987 | Brophy et al. |
| 4,654,449 A | 3/1987 | Chang et al. |
| 4,655,893 A | 4/1987 | Beale |
| 4,658,073 A | 4/1987 | Tabak |
| 4,658,077 A | 4/1987 | Kolts et al. |
| 4,665,259 A | 5/1987 | Brazdil et al. |
| 4,665,267 A | 5/1987 | Barri |
| 4,665,270 A | 5/1987 | Brophy et al. |
| 4,675,410 A | 6/1987 | Feitler et al. |
| 4,690,903 A | 9/1987 | Chen et al. |
| 4,695,663 A | 9/1987 | Hall et al. |
| 4,696,985 A | 9/1987 | Martin |
| 4,704,488 A | 11/1987 | Devries et al. |
| 4,704,493 A | 11/1987 | Devries et al. |
| 4,709,108 A | 11/1987 | Devries et al. |
| 4,720,600 A | 1/1988 | Beech, Jr. et al. |
| 4,720,602 A | 1/1988 | Chu |
| 4,724,275 A | 2/1988 | Hinnenkamp et al. |
| 4,725,425 A | 2/1988 | Lesher et al. |
| 4,735,747 A | 4/1988 | Ollivier et al. |
| 4,737,594 A | 4/1988 | Olah |
| 4,748,013 A | 5/1988 | Saito et al. |
| 4,762,596 A | 8/1988 | Huang et al. |
| 4,769,504 A | 9/1988 | Noceti et al. |
| 4,774,216 A | 9/1988 | Kolts et al. |
| 4,775,462 A | 10/1988 | Imai et al. |
| 4,777,321 A | 10/1988 | Harandi et al. |
| 4,781,733 A | 11/1988 | Babcock et al. |
| 4,783,566 A | 11/1988 | Kocal et al. |
| 4,788,369 A | 11/1988 | Marsh et al. |
| 4,788,377 A | 11/1988 | Chang et al. |
| 4,792,642 A | 12/1988 | Rule et al. |
| 4,795,732 A | 1/1989 | Barri |
| 4,795,737 A | 1/1989 | Rule et al. |
| 4,795,843 A | 1/1989 | Imai et al. |
| 4,795,848 A | 1/1989 | Teller et al. |
| 4,804,797 A | 2/1989 | Minet et al. |
| 4,804,800 A | 2/1989 | Bortinger et al. |
| 4,808,763 A | 2/1989 | Shum |
| 4,814,527 A | 3/1989 | Diesen |
| 4,814,532 A | 3/1989 | Yoshida et al. |
| 4,814,535 A | 3/1989 | Yurchak |
| 4,814,536 A | 3/1989 | Yurchak |
| 4,849,562 A | 7/1989 | Buhs et al. |
| 4,849,573 A | 7/1989 | Kaefing |
| 4,851,602 A | 7/1989 | Harandi et al. |
| 4,851,606 A | 7/1989 | Ragonese et al. |
| 4,886,925 A | 12/1989 | Harandi |
| 4,886,932 A | 12/1989 | Leyshon |
| 4,891,463 A | 1/1990 | Chu |
| 4,895,995 A | 1/1990 | James, Jr. et al. |
| 4,899,000 A | 2/1990 | Stauffer |
| 4,899,001 A | 2/1990 | Kalnes et al. |
| 4,899,002 A | 2/1990 | Harandi et al. |
| 4,902,842 A | 2/1990 | Kalnes et al. |
| 4,925,995 A | 5/1990 | Robschlager |
| 4,929,781 A | 5/1990 | James, Jr. et al. |
| 4,939,310 A | 7/1990 | Wade |
| 4,939,311 A | 7/1990 | Washecheck et al. |
| 4,939,314 A | 7/1990 | Harandi et al. |
| 4,945,175 A | 7/1990 | Hobbs et al. |
| 4,950,811 A | 8/1990 | Doussain et al. |
| 4,950,822 A | 8/1990 | Dileo et al. |
| 4,956,521 A | 9/1990 | Volles |
| 4,962,252 A | 10/1990 | Wade |
| 4,973,776 A | 11/1990 | Allenger et al. |
| 4,973,786 A | 11/1990 | Karra |
| 4,982,024 A | 1/1991 | Lin et al. |
| 4,982,041 A | 1/1991 | Campbell |
| 4,988,660 A | 1/1991 | Campbell |
| 4,990,696 A | 2/1991 | Stauffer |
| 4,990,711 A | 2/1991 | Chen et al. |
| 5,001,293 A | 3/1991 | Nubel et al. |
| 5,004,847 A | 4/1991 | Beaver et al. |
| 5,013,424 A | 5/1991 | James, Jr. et al. |
| 5,013,793 A | 5/1991 | Wang et al. |
| 5,019,652 A | 5/1991 | Taylor et al. |
| 5,026,934 A | 6/1991 | Bains et al. |
| 5,026,937 A | 6/1991 | Bricker |
| 5,026,944 A | 6/1991 | Allenger et al. |
| 5,034,566 A | 7/1991 | Ishino et al. |
| 5,043,502 A | 8/1991 | Martindale et al. |
| 5,055,235 A | 10/1991 | Brackenridge et al. |
| 5,055,625 A | 10/1991 | Neidiffer et al. |
| 5,055,633 A | 10/1991 | Volles |
| 5,055,634 A | 10/1991 | Volles |
| 5,059,744 A | 10/1991 | Harandi et al. |
| 5,068,478 A | 11/1991 | Miller et al. |
| 5,071,449 A | 12/1991 | Sircar |
| 5,071,815 A | 12/1991 | Wallace et al. |
| 5,073,656 A | 12/1991 | Chafin et al. |
| 5,073,657 A | 12/1991 | Warren |
| 5,082,473 A | 1/1992 | Keefer |
| 5,082,816 A | 1/1992 | Teller et al. |
| 5,085,674 A | 2/1992 | Leavitt |
| 5,087,779 A | 2/1992 | Nubel et al. |
| 5,087,786 A | 2/1992 | Nubel et al. |
| 5,087,787 A | 2/1992 | Kimble et al. |
| 5,093,533 A | 3/1992 | Wilson |
| 5,093,542 A | 3/1992 | Gaffney |
| 5,096,469 A | 3/1992 | Keefer |
| 5,097,083 A | 3/1992 | Stauffer |
| 5,099,084 A | 3/1992 | Stauffer |
| 5,105,045 A | 4/1992 | Kimble et al. |
| 5,105,046 A | 4/1992 | Washecheck |
| 5,107,032 A | 4/1992 | Erb et al. |
| 5,107,051 A | 4/1992 | Pannell |
| 5,107,061 A | 4/1992 | Ou et al. |
| 5,108,579 A | 4/1992 | Casci |
| 5,118,899 A | 6/1992 | Kimble et al. |
| 5,120,332 A | 6/1992 | Wells |
| 5,132,343 A | 7/1992 | Zwecker et al. |
| 5,138,112 A | 8/1992 | Gosling et al. |
| 5,139,991 A | 8/1992 | Taylor et al. |
| 5,146,027 A | 9/1992 | Gaffney |
| 5,157,189 A | 10/1992 | Karra |
| 5,160,502 A | 11/1992 | Kimble et al. |
| 5,166,452 A | 11/1992 | Gradl et al. |
| 5,175,382 A | 12/1992 | Hebgen et al. |
| 5,178,748 A | 1/1993 | Casci et al. |
| 5,185,479 A | 2/1993 | Stauffer |
| 5,188,725 A | 2/1993 | Harandi |
| 5,191,142 A | 3/1993 | Marshall et al. |
| 5,194,244 A | 3/1993 | Brownscombe et al. |
| 5,202,506 A | 4/1993 | Kirchner et al. |
| 5,202,511 A | 4/1993 | Salinas, III et al. |
| 5,208,402 A | 5/1993 | Wilson |
| 5,210,357 A | 5/1993 | Kolts et al. |
| 5,215,648 A | 6/1993 | Zones et al. |
| 5,223,471 A | 6/1993 | Washecheck |
| 5,228,888 A | 7/1993 | Gmelin et al. |
| 5,233,113 A | 8/1993 | Periana et al. |
| 5,237,115 A | 8/1993 | Makovec et al. |

(56) References Cited

U.S. PATENT DOCUMENTS

| | | |
|---|---|---|
| 5,243,098 A | 9/1993 | Miller et al. |
| 5,243,114 A | 9/1993 | Johnson et al. |
| 5,245,109 A | 9/1993 | Kaminsky et al. |
| 5,254,772 A | 10/1993 | Dukat et al. |
| 5,254,790 A | 10/1993 | Thomas et al. |
| 5,264,635 A | 11/1993 | Le et al. |
| 5,268,518 A | 12/1993 | West et al. |
| 5,276,226 A | 1/1994 | Horvath et al. |
| 5,276,240 A | 1/1994 | Timmons et al. |
| 5,276,242 A | 1/1994 | Wu |
| 5,284,990 A | 2/1994 | Peterson et al. |
| 5,300,126 A | 4/1994 | Brown et al. |
| 5,306,855 A | 4/1994 | Periana et al. |
| 5,316,995 A | 5/1994 | Kaminsky et al. |
| 5,319,132 A | 6/1994 | Ozawa et al. |
| 5,334,777 A | 8/1994 | Miller et al. |
| 5,345,021 A | 9/1994 | Casci et al. |
| 5,354,916 A | 10/1994 | Horvath et al. |
| 5,354,931 A | 10/1994 | Jan et al. |
| 5,358,645 A | 10/1994 | Hong et al. |
| 5,366,949 A | 11/1994 | Schubert |
| 5,371,313 A | 12/1994 | Ostrowicki |
| 5,382,704 A | 1/1995 | Krespan et al. |
| 5,382,743 A | 1/1995 | Beech, Jr. et al. |
| 5,382,744 A | 1/1995 | Abbott et al. |
| 5,385,650 A | 1/1995 | Howarth et al. |
| 5,385,718 A | 1/1995 | Casci et al. |
| 5,395,981 A | 3/1995 | Marker |
| 5,399,258 A | 3/1995 | Fletcher et al. |
| 5,401,890 A | 3/1995 | Parks |
| 5,401,894 A | 3/1995 | Brasier et al. |
| 5,406,017 A | 4/1995 | Withers, Jr. |
| 5,411,641 A | 5/1995 | Trainham, III et al. |
| 5,414,173 A | 5/1995 | Garces et al. |
| 5,430,210 A | 7/1995 | Grasselli et al. |
| 5,430,214 A | 7/1995 | Smith et al. |
| 5,430,219 A | 7/1995 | Sanfilippo et al. |
| 5,433,828 A | 7/1995 | van Velzen et al. |
| 5,436,378 A | 7/1995 | Masini et al. |
| 5,444,168 A | 8/1995 | Brown |
| 5,446,234 A | 8/1995 | Casci et al. |
| 5,453,557 A | 9/1995 | Harley et al. |
| 5,456,822 A | 10/1995 | Marcilly et al. |
| 5,457,255 A | 10/1995 | Kumata et al. |
| 5,464,799 A | 11/1995 | Casci et al. |
| 5,465,699 A | 11/1995 | Voigt |
| 5,470,377 A | 11/1995 | Whitlock |
| 5,480,629 A | 1/1996 | Thompson et al. |
| 5,486,627 A | 1/1996 | Quarderer, Jr. et al. |
| 5,489,719 A | 2/1996 | Le et al. |
| 5,489,727 A | 2/1996 | Randolph et al. |
| 5,500,297 A | 3/1996 | Thompson et al. |
| 5,510,525 A | 4/1996 | Sen et al. |
| 5,523,503 A | 6/1996 | Funk et al. |
| 5,525,230 A | 6/1996 | Wrigley et al. |
| 5,538,540 A | 7/1996 | Whitlock |
| 5,563,313 A | 10/1996 | Chung et al. |
| 5,565,092 A | 10/1996 | Pannell et al. |
| 5,565,616 A | 10/1996 | Li et al. |
| 5,571,762 A | 11/1996 | Clerici et al. |
| 5,571,885 A | 11/1996 | Chung et al. |
| 5,599,381 A | 2/1997 | Whitlock |
| 5,600,043 A | 2/1997 | Johnston et al. |
| 5,600,045 A | 2/1997 | Van Der Aalst et al. |
| 5,609,654 A | 3/1997 | Le et al. |
| 5,633,419 A | 5/1997 | Spencer et al. |
| 5,639,930 A | 6/1997 | Penick |
| 5,653,956 A | 8/1997 | Zones |
| 5,656,149 A | 8/1997 | Zones et al. |
| 5,661,097 A | 8/1997 | Spencer et al. |
| 5,663,465 A | 9/1997 | Clegg et al. |
| 5,663,474 A | 9/1997 | Pham et al. |
| 5,674,464 A | 10/1997 | Van Velzen et al. |
| 5,675,046 A | 10/1997 | Ohno et al. |
| 5,675,052 A | 10/1997 | Menon et al. |
| 5,679,134 A | 10/1997 | Brugerolle et al. |
| 5,679,879 A | 10/1997 | Mercier et al. |
| 5,684,213 A | 11/1997 | Nemphos et al. |
| 5,693,191 A | 12/1997 | Pividal et al. |
| 5,695,890 A | 12/1997 | Thompson et al. |
| 5,698,747 A | 12/1997 | Godwin et al. |
| 5,705,712 A | 1/1998 | Frey et al. |
| 5,705,728 A | 1/1998 | Viswanathan et al. |
| 5,705,729 A | 1/1998 | Huang |
| 5,708,246 A | 1/1998 | Camaioni et al. |
| 5,720,858 A | 2/1998 | Noceti et al. |
| 5,728,897 A | 3/1998 | Buysch et al. |
| 5,728,905 A | 3/1998 | Clegg et al. |
| 5,734,073 A | 3/1998 | Chambers et al. |
| 5,741,949 A | 4/1998 | Mack |
| 5,744,669 A | 4/1998 | Kalnes et al. |
| 5,750,801 A | 5/1998 | Buysch et al. |
| 5,770,175 A | 6/1998 | Zones |
| 5,776,871 A | 7/1998 | Cothran et al. |
| 5,780,703 A | 7/1998 | Chang et al. |
| 5,782,936 A | 7/1998 | Riley |
| 5,798,314 A | 8/1998 | Spencer et al. |
| 5,814,715 A | 9/1998 | Chen et al. |
| 5,817,904 A | 10/1998 | Vic et al. |
| 5,821,394 A | 10/1998 | Schoebrechts et al. |
| 5,847,224 A | 12/1998 | Koga et al. |
| 5,849,978 A | 12/1998 | Benazzi et al. |
| 5,866,735 A | 2/1999 | Cheung et al. |
| 5,882,614 A | 3/1999 | Taylor, Jr. et al. |
| 5,895,831 A | 4/1999 | Brasier et al. |
| 5,898,086 A | 4/1999 | Harris |
| 5,905,169 A | 5/1999 | Jacobson |
| 5,906,892 A | 5/1999 | Thompson et al. |
| 5,908,963 A | 6/1999 | Voss et al. |
| 5,928,488 A | 7/1999 | Newman |
| 5,952,538 A | 9/1999 | Vaughn et al. |
| 5,959,170 A | 9/1999 | Withers, Jr. et al. |
| 5,968,236 A | 10/1999 | Bassine |
| 5,969,195 A | 10/1999 | Stabel et al. |
| 5,977,402 A | 11/1999 | Sekiguchi et al. |
| 5,983,476 A | 11/1999 | Eshelman et al. |
| 5,986,158 A | 11/1999 | Van Broekhoven et al. |
| 5,994,604 A | 11/1999 | Reagen et al. |
| 5,998,679 A | 12/1999 | Miller et al. |
| 5,998,686 A | 12/1999 | Clem et al. |
| 6,002,059 A | 12/1999 | Hellring et al. |
| 6,015,867 A | 1/2000 | Fushimi et al. |
| 6,018,088 A | 1/2000 | Olah |
| 6,022,929 A | 2/2000 | Chen et al. |
| 6,034,288 A | 3/2000 | Scott et al. |
| 6,056,804 A | 5/2000 | Keefer et al. |
| 6,068,679 A | 5/2000 | Zheng |
| 6,072,091 A | 6/2000 | Cosyns et al. |
| 6,087,294 A | 7/2000 | Klabunde et al. |
| 6,090,312 A | 7/2000 | Ziaka et al. |
| 6,093,306 A | 7/2000 | Hanrahan et al. |
| 6,096,932 A | 8/2000 | Subramanian |
| 6,096,933 A | 8/2000 | Cheung et al. |
| 6,103,215 A | 8/2000 | Zones et al. |
| 6,107,561 A | 8/2000 | Thompson et al. |
| 6,117,371 A | 9/2000 | Mack |
| 6,124,514 A | 9/2000 | Emmrich et al. |
| 6,127,588 A | 10/2000 | Kimble et al. |
| 6,130,260 A | 10/2000 | Hall et al. |
| 6,143,939 A | 11/2000 | Farcasiu et al. |
| 6,169,218 B1 | 1/2001 | Hearn et al. |
| 6,180,841 B1 | 1/2001 | Fatutto et al. |
| 6,187,871 B1 | 2/2001 | Thompson et al. |
| 6,187,983 B1 | 2/2001 | Sun |
| 6,203,712 B1 | 3/2001 | Bronner et al. |
| 6,207,864 B1 | 3/2001 | Henningsen et al. |
| 6,225,517 B1 | 5/2001 | Nascimento et al. |
| 6,248,218 B1 | 6/2001 | Linkous et al. |
| 6,265,505 B1 | 7/2001 | McConville et al. |
| 6,281,405 B1 | 8/2001 | Davis et al. |
| 6,320,085 B1 | 11/2001 | Arvai et al. |
| 6,337,063 B1 | 1/2002 | Rouleau et al. |
| 6,342,200 B1 | 1/2002 | Rouleau et al. |
| 6,368,490 B1 | 4/2002 | Gestermann |

(56) References Cited

U.S. PATENT DOCUMENTS

| | | | |
|---|---|---|---|
| 6,369,283 B1 | 4/2002 | Guram et al. |
| 6,372,949 B1 | 4/2002 | Brown et al. |
| 6,376,731 B1 | 4/2002 | Evans et al. |
| 6,380,328 B1 | 4/2002 | McConville et al. |
| 6,380,423 B2 | 4/2002 | Banning et al. |
| 6,380,444 B1 | 4/2002 | Bjerrum et al. |
| 6,395,945 B1 | 5/2002 | Randolph |
| 6,403,840 B1 | 6/2002 | Zhou et al. |
| 6,406,523 B1 | 6/2002 | Connor et al. |
| 6,423,211 B1 | 7/2002 | Randolph et al. |
| 6,426,441 B1 | 7/2002 | Randolph et al. |
| 6,426,442 B1 | 7/2002 | Ichikawa et al. |
| 6,452,058 B1 | 9/2002 | Schweizer et al. |
| 6,455,650 B1 | 9/2002 | Lipian et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,345 B2 | 10/2002 | Hintermann et al. |
| 6,472,572 B1 | 10/2002 | Zhou et al. |
| 6,475,463 B1 | 11/2002 | Elomari et al. |
| 6,475,464 B1 | 11/2002 | Rouleau et al. |
| 6,479,705 B2 | 11/2002 | Murata et al. |
| 6,482,997 B2 | 11/2002 | Petit-Clair et al. |
| 6,486,368 B1 | 11/2002 | Zhou et al. |
| 6,491,809 B1 | 12/2002 | Briot et al. |
| 6,495,484 B1 | 12/2002 | Holtcamp |
| 6,509,485 B2 | 1/2003 | Mul et al. |
| 6,511,526 B2 | 1/2003 | Jagger et al. |
| 6,514,319 B2 | 2/2003 | Keefer et al. |
| 6,518,474 B1 | 2/2003 | Sanderson et al. |
| 6,518,476 B1 | 2/2003 | Culp et al. |
| 6,525,228 B2 | 2/2003 | Chauvin et al. |
| 6,525,230 B2 | 2/2003 | Grosso |
| 6,528,693 B1 | 3/2003 | Gandy et al. |
| 6,538,162 B2 | 3/2003 | Chang et al. |
| 6,540,905 B1 | 4/2003 | Elomari |
| 6,545,191 B1 | 4/2003 | Stauffer |
| 6,547,958 B1 | 4/2003 | Elomari |
| 6,548,040 B1 | 4/2003 | Rouleau et al. |
| 6,552,241 B1 | 4/2003 | Randolph et al. |
| 6,566,572 B2 | 5/2003 | Okamoto et al. |
| 6,572,829 B2 | 6/2003 | Linkous et al. |
| 6,585,953 B2 | 7/2003 | Roberts et al. |
| 6,616,830 B2 | 9/2003 | Elomari |
| 6,620,757 B2 | 9/2003 | McConville et al. |
| 6,627,777 B2 | 9/2003 | Rossi et al. |
| 6,632,971 B2 | 10/2003 | Brown et al. |
| 6,635,793 B2 | 10/2003 | Mul et al. |
| 6,641,644 B2 | 11/2003 | Jagger et al. |
| 6,646,102 B2 | 11/2003 | Boriack et al. |
| 6,669,846 B2 | 12/2003 | Perriello |
| 6,672,572 B2 | 1/2004 | Werlen |
| 6,679,986 B1 | 1/2004 | Da Silva et al. |
| 6,680,415 B1 | 1/2004 | Gulotty, Jr. et al. |
| 6,692,626 B2 | 2/2004 | Keefer et al. |
| 6,692,723 B2 | 2/2004 | Rouleau et al. |
| 6,710,213 B2 | 3/2004 | Aoki et al. |
| 6,713,087 B2 | 3/2004 | Tracy et al. |
| 6,713,655 B2 | 3/2004 | Yilmaz et al. |
| RE38,493 E | 4/2004 | Keefer et al. |
| 6,723,808 B2 | 4/2004 | Holtcamp |
| 6,727,400 B2 | 4/2004 | Messier et al. |
| 6,740,146 B2 | 5/2004 | Simonds |
| 6,753,390 B2 | 6/2004 | Ehrman et al. |
| 6,765,120 B2 | 7/2004 | Weber et al. |
| 6,797,845 B1 | 9/2004 | Hickman et al. |
| 6,797,851 B2 | 9/2004 | Martens et al. |
| 6,821,924 B2 | 11/2004 | Gulotty, Jr. et al. |
| 6,822,123 B2 | 11/2004 | Stauffer |
| 6,822,125 B2 | 11/2004 | Lee et al. |
| 6,825,307 B2 | 11/2004 | Goodall |
| 6,825,383 B1 | 11/2004 | Dewkar et al. |
| 6,831,032 B2 | 12/2004 | Spaether |
| 6,838,576 B1 | 1/2005 | Wicki et al. |
| 6,841,063 B2 | 1/2005 | Elomari |
| 6,852,896 B2 | 2/2005 | Stauffer |
| 6,866,950 B2 | 3/2005 | Connor et al. |
| 6,869,903 B2 | 3/2005 | Matsunaga |
| 6,875,339 B2 | 4/2005 | Rangarajan et al. |
| 6,878,853 B2 | 4/2005 | Tanaka et al. |
| 6,888,013 B2 | 5/2005 | Paparatto et al. |
| 6,900,363 B2 | 5/2005 | Harth et al. |
| 6,902,602 B2 | 6/2005 | Keefer et al. |
| 6,903,171 B2 | 6/2005 | Rhodes et al. |
| 6,909,024 B1 | 6/2005 | Jones et al. |
| 6,921,597 B2 | 7/2005 | Keefer et al. |
| 6,933,417 B1 | 8/2005 | Henley et al. |
| 6,946,566 B2 | 9/2005 | Yaegashi et al. |
| 6,953,868 B2 | 10/2005 | Boaen et al. |
| 6,953,870 B2 | 10/2005 | Yan et al. |
| 6,953,873 B2 | 10/2005 | Cortright et al. |
| 6,956,140 B2 | 10/2005 | Ehrenfeld |
| 6,958,306 B2 | 10/2005 | Holtcamp |
| 6,984,763 B2 | 1/2006 | Schweizer et al. |
| 7,001,872 B2 | 2/2006 | Pyecroft et al. |
| 7,002,050 B2 | 2/2006 | Santiago Fernandez et al. |
| 7,011,811 B2 | 3/2006 | Elomari |
| 7,019,182 B2 | 3/2006 | Grosso |
| 7,026,145 B2 | 4/2006 | Mizrahi et al. |
| 7,026,519 B2 | 4/2006 | Santiago Fernandez et al. |
| 7,037,358 B2 | 5/2006 | Babicki et al. |
| 7,045,111 B1 | 5/2006 | DeGroot et al. |
| 7,045,670 B2 | 5/2006 | Johnson et al. |
| 7,049,388 B2 | 5/2006 | Boriack et al. |
| 7,053,252 B2 | 5/2006 | Boussand et al. |
| 7,057,081 B2 | 6/2006 | Allison et al. |
| 7,060,865 B2 | 6/2006 | Ding et al. |
| 7,064,238 B2 | 6/2006 | Waycuilis |
| 7,064,240 B2 | 6/2006 | Ohno et al. |
| 7,067,448 B1 | 6/2006 | Weitkamp et al. |
| 7,083,714 B2 | 8/2006 | Elomari |
| 7,084,308 B1 | 8/2006 | Stauffer |
| 7,091,270 B2 | 8/2006 | Zilberman et al. |
| 7,091,387 B2 | 8/2006 | Fong et al. |
| 7,091,391 B2 | 8/2006 | Stauffer |
| 7,094,936 B1 | 8/2006 | Owens et al. |
| 7,098,371 B2 | 8/2006 | Mack et al. |
| 7,105,710 B2 | 9/2006 | Boons et al. |
| 7,138,534 B2 | 11/2006 | Forlin et al. |
| 7,141,708 B2 | 11/2006 | Marsella et al. |
| 7,145,045 B2 | 12/2006 | Harmsen et al. |
| 7,148,356 B2 | 12/2006 | Smith, III et al. |
| 7,148,390 B2 * | 12/2006 | Zhou et al. .................. 585/324 |
| 7,151,199 B2 | 12/2006 | Martens et al. |
| 7,161,050 B2 | 1/2007 | Sherman et al. |
| 7,169,730 B2 | 1/2007 | Ma et al. |
| 7,176,340 B2 | 2/2007 | Van Broekhoven et al. |
| 7,176,342 B2 | 2/2007 | Bellussi et al. |
| 7,182,871 B2 | 2/2007 | Perriello |
| 7,193,093 B2 | 3/2007 | Murray et al. |
| 7,196,239 B2 | 3/2007 | Van Egmond et al. |
| 7,199,083 B2 | 4/2007 | Zevallos |
| 7,199,255 B2 | 4/2007 | Murray et al. |
| 7,208,641 B2 | 4/2007 | Nagasaki et al. |
| 7,214,750 B2 | 5/2007 | McDonald et al. |
| 7,220,391 B1 | 5/2007 | Huang et al. |
| 7,226,569 B2 | 6/2007 | Elomari |
| 7,226,576 B2 | 6/2007 | Elomari |
| 7,230,150 B2 | 6/2007 | Grosso et al. |
| 7,230,151 B2 | 6/2007 | Martens et al. |
| 7,232,872 B2 | 6/2007 | Shaffer et al. |
| 7,238,846 B2 | 7/2007 | Janssen et al. |
| 7,244,795 B2 | 7/2007 | Agapiou et al. |
| 7,244,867 B2 | 7/2007 | Waycuilis |
| 7,250,107 B2 | 7/2007 | Benazzi et al. |
| 7,250,542 B2 | 7/2007 | Smith, Jr. et al. |
| 7,252,920 B2 | 8/2007 | Kurokawa et al. |
| 7,253,327 B2 | 8/2007 | Janssens et al. |
| 7,253,328 B2 | 8/2007 | Stauffer |
| 7,265,193 B2 | 9/2007 | Weng et al. |
| 7,267,758 B2 | 9/2007 | Benazzi et al. |
| 7,268,263 B1 | 9/2007 | Frey et al. |
| 7,271,303 B1 | 9/2007 | Sechrist et al. |
| 7,273,957 B2 | 9/2007 | Bakshi et al. |

(56) References Cited

U.S. PATENT DOCUMENTS

| | | | |
|---|---|---|---|
| 7,282,603 B2 | 10/2007 | Richards | |
| 7,285,698 B2 | 10/2007 | Liu et al. | |
| 7,304,193 B1 | 12/2007 | Frey et al. | |
| 7,342,144 B2 | 3/2008 | Kaizik et al. | |
| 7,348,295 B2 | 3/2008 | Zones et al. | |
| 7,348,464 B2 | 3/2008 | Waycuilis | |
| 7,357,904 B2 | 4/2008 | Zones et al. | |
| 7,361,794 B2 | 4/2008 | Grosso | |
| 7,365,102 B1 | 4/2008 | Weissman | |
| 7,390,395 B2 | 6/2008 | Elomari | |
| 7,560,607 B2 | 7/2009 | Waycuilis | |
| 7,674,941 B2 * | 3/2010 | Waycuilis et al. | 585/408 |
| 7,713,510 B2 | 5/2010 | Harrod et al. | |
| 7,880,041 B2 | 2/2011 | Waycuilis | |
| 8,008,535 B2 | 8/2011 | Waycuilis | |
| 8,173,851 B2 * | 5/2012 | Waycuilis et al. | 585/408 |
| 8,198,495 B2 * | 6/2012 | Waycuilis et al. | 585/408 |
| 8,232,441 B2 | 7/2012 | Waycuilis | |
| 8,282,810 B2 | 10/2012 | Waycuilis | |
| 8,367,884 B2 * | 2/2013 | Waycuilis | 585/359 |
| 8,373,015 B2 * | 2/2013 | Stark et al. | 585/733 |
| 8,415,517 B2 * | 4/2013 | Gadewar et al. | 585/310 |
| 8,436,220 B2 | 5/2013 | Kurukchi et al. | |
| 8,449,849 B2 * | 5/2013 | Gadewar et al. | 422/630 |
| 8,642,822 B2 | 2/2014 | Brickey et al. | |
| 2001/0051662 A1 | 12/2001 | Arcuri et al. | |
| 2002/0102672 A1 | 8/2002 | Mizrahi | |
| 2002/0193649 A1 | 12/2002 | O'Rear et al. | |
| 2002/0198416 A1 | 12/2002 | Zhou et al. | |
| 2003/0004380 A1 | 1/2003 | Grumann | |
| 2003/0065239 A1 | 4/2003 | Zhu | |
| 2003/0069452 A1 | 4/2003 | Sherman et al. | |
| 2003/0078456 A1 | 4/2003 | Yilmaz et al. | |
| 2003/0120121 A1 | 6/2003 | Sherman et al. | |
| 2003/0125589 A1 | 7/2003 | Grosso | |
| 2003/0166973 A1 | 9/2003 | Zhou et al. | |
| 2004/0006246 A1 | 1/2004 | Sherman et al. | |
| 2004/0055955 A1 | 3/2004 | Davis | |
| 2004/0062705 A1 | 4/2004 | Leduc | |
| 2004/0152929 A1 | 8/2004 | Clarke | |
| 2004/0158107 A1 | 8/2004 | Aoki | |
| 2004/0158108 A1 | 8/2004 | Snoble | |
| 2004/0171779 A1 | 9/2004 | Matyjaszewski et al. | |
| 2004/0187684 A1 | 9/2004 | Elomari | |
| 2004/0188271 A1 | 9/2004 | Ramachandraiah et al. | |
| 2004/0188324 A1 | 9/2004 | Elomari | |
| 2004/0220433 A1 | 11/2004 | Van Der Heide | |
| 2005/0027084 A1 | 2/2005 | Clarke | |
| 2005/0038310 A1 | 2/2005 | Lorkovic et al. | |
| 2005/0042159 A1 | 2/2005 | Elomari | |
| 2005/0047927 A1 | 3/2005 | Lee et al. | |
| 2005/0148805 A1 | 7/2005 | Jones | |
| 2005/0171393 A1 | 8/2005 | Lorkovic | |
| 2005/0192468 A1 | 9/2005 | Sherman et al. | |
| 2005/0215837 A1 | 9/2005 | Hoffpauir | |
| 2005/0218041 A1 | 10/2005 | Yoshida et al. | |
| 2005/0234276 A1 | 10/2005 | Waycuilis | |
| 2005/0234277 A1 | 10/2005 | Waycuilis | |
| 2005/0245771 A1 | 11/2005 | Fong et al. | |
| 2005/0245772 A1 | 11/2005 | Fong | |
| 2005/0245777 A1 | 11/2005 | Fong | |
| 2005/0267224 A1 | 12/2005 | Herling | |
| 2006/0025617 A1 | 2/2006 | Begley | |
| 2006/0100469 A1 | 5/2006 | Waycuilis | |
| 2006/0135823 A1 | 6/2006 | Jun | |
| 2006/0138025 A1 | 6/2006 | Zones | |
| 2006/0138026 A1 | 6/2006 | Chen | |
| 2006/0149116 A1 | 7/2006 | Slaugh | |
| 2006/0229228 A1 | 10/2006 | Komon et al. | |
| 2006/0229475 A1 | 10/2006 | Weiss et al. | |
| 2006/0270863 A1 | 11/2006 | Reiling | |
| 2006/0288690 A1 | 12/2006 | Elomari | |
| 2007/0004955 A1 | 1/2007 | Kay | |
| 2007/0078285 A1 | 4/2007 | Dagle | |
| 2007/0100189 A1 | 5/2007 | Stauffer | |
| 2007/0129584 A1 | 6/2007 | Basset | |
| 2007/0142680 A1 | 6/2007 | Ayoub | |
| 2007/0148067 A1 | 6/2007 | Zones | |
| 2007/0148086 A1 | 6/2007 | Zones | |
| 2007/0149778 A1 | 6/2007 | Zones | |
| 2007/0149789 A1 | 6/2007 | Zones | |
| 2007/0149819 A1 | 6/2007 | Zones | |
| 2007/0149824 A1 | 6/2007 | Zones | |
| 2007/0149837 A1 | 6/2007 | Zones | |
| 2007/0149838 A1 | 6/2007 | Chretien | |
| 2007/0197801 A1 | 8/2007 | Bolk | |
| 2007/0197847 A1 | 8/2007 | Liu | |
| 2007/0213545 A1 | 9/2007 | Bolk | |
| 2007/0238905 A1 | 10/2007 | Arredondo | |
| 2007/0238909 A1 | 10/2007 | Gadewar et al. | |
| 2007/0276168 A1 | 11/2007 | Garel | |
| 2007/0284284 A1 | 12/2007 | Zones | |
| 2008/0022717 A1 | 1/2008 | Yoshida et al. | |
| 2008/0152555 A1 | 6/2008 | Wang et al. | |
| 2008/0171898 A1 | 7/2008 | Waycuilis | |
| 2008/0183022 A1 | 7/2008 | Waycuilis | |
| 2008/0188697 A1 | 8/2008 | Lorkovic | |
| 2008/0200740 A1 | 8/2008 | Waycuilis | |
| 2008/0210596 A1 | 9/2008 | Litt et al. | |
| 2008/0275279 A1 | 11/2008 | Podkolzin et al. | |
| 2008/0275284 A1 | 11/2008 | Waycuilis | |
| 2008/0314758 A1 | 12/2008 | Grosso et al. | |
| 2009/0005620 A1 | 1/2009 | Waycuilis et al. | |
| 2009/0163749 A1 | 6/2009 | Li et al. | |
| 2009/0247796 A1 | 10/2009 | Waycuilis et al. | |
| 2009/0270655 A1 | 10/2009 | Fong et al. | |
| 2009/0306443 A1 | 12/2009 | Stark et al. | |
| 2009/0308759 A1 | 12/2009 | Waycuilis | |
| 2009/0312586 A1 | 12/2009 | Waycuilis et al. | |
| 2009/0326292 A1 | 12/2009 | Waycuilis | |
| 2010/0030005 A1 | 2/2010 | Sauer et al. | |
| 2010/0087686 A1 | 4/2010 | Fong et al. | |
| 2010/0096588 A1 | 4/2010 | Gadewar et al. | |
| 2010/0099929 A1 | 4/2010 | Gadewar | |
| 2010/0099930 A1 | 4/2010 | Stoimenov et al. | |
| 2010/0105972 A1 | 4/2010 | Lorkovic | |
| 2010/0234637 A1 | 9/2010 | Fong et al. | |
| 2010/0270167 A1 | 10/2010 | McFarland | |
| 2011/0015458 A1 | 1/2011 | Waycuilis et al. | |
| 2011/0071326 A1 | 3/2011 | Waycuilis | |
| 2011/0198285 A1 | 8/2011 | Wallace | |
| 2011/0218372 A1 * | 9/2011 | Waycuilis et al. | 585/300 |
| 2011/0218374 A1 | 9/2011 | Waycuilis | |
| 2012/0141356 A1 | 6/2012 | Brickey et al. | |
| 2012/0245399 A1 | 9/2012 | Kurukchi et al. | |
| 2012/0313034 A1 | 12/2012 | Kurukchi et al. | |
| 2013/0006024 A1 | 1/2013 | Kurukchi et al. | |
| 2013/0046121 A1 | 2/2013 | Kurukchi et al. | |
| 2013/0079564 A1 | 3/2013 | Waycuilis | |
| 2013/0090504 A1 | 4/2013 | Roscoe et al. | |
| 2013/0102820 A1 * | 4/2013 | Waycuilis et al. | 585/302 |
| 2013/0156681 A1 | 6/2013 | Kurukchi et al. | |
| 2013/0158324 A1 | 6/2013 | Waycuilis et al. | |
| 2013/0178675 A1 | 7/2013 | Kurukchi et al. | |
| 2013/0217938 A1 | 8/2013 | Waycuilis et al. | |

FOREIGN PATENT DOCUMENTS

| | | |
|---|---|---|
| CA | 1202610 | 4/1986 |
| CA | 2542857 | 5/2005 |
| CA | 2236126 | 8/2006 |
| CA | 2203115 | 9/2006 |
| CA | 2510093 | 12/2006 |
| CA | 2641348 A1 | 8/2007 |
| CA | 2684765 A1 | 11/2008 |
| EP | 0164798 A1 | 12/1985 |
| EP | 0418971 A1 | 3/1991 |
| EP | 0418974 A1 | 3/1991 |
| EP | 0418975 A1 | 3/1991 |
| EP | 0510238 A1 | 10/1992 |
| EP | 0526908 A2 | 2/1993 |
| EP | 0346612 B1 | 8/1993 |
| EP | 0560546 A1 | 9/1993 |
| EP | 0976705 A1 | 2/2000 |

(56) References Cited

FOREIGN PATENT DOCUMENTS

| | | |
|---|---|---|
| EP | 1186591 A2 | 3/2002 |
| EP | 1253126 A1 | 10/2002 |
| EP | 1312411 A2 | 5/2003 |
| EP | 1235769 B1 | 5/2004 |
| EP | 1435349 A2 | 7/2004 |
| EP | 1440939 A1 | 7/2004 |
| EP | 1235772 B1 | 1/2005 |
| EP | 1661620 A1 | 5/2006 |
| EP | 1760057 A1 | 3/2007 |
| EP | 1689728 B1 | 4/2007 |
| EP | 1808227 A1 | 7/2007 |
| EP | 1837320 A1 | 9/2007 |
| GB | 5125 | 0/1912 |
| GB | 156122 | 3/1922 |
| GB | 294100 | 6/1929 |
| GB | 363009 | 12/1931 |
| GB | 402928 | 12/1933 |
| GB | 474922 A | 11/1937 |
| GB | 536491 | 5/1941 |
| GB | 553950 | 6/1943 |
| GB | 586483 | 3/1947 |
| GB | 775590 | 5/1957 |
| GB | 793214 | 4/1958 |
| GB | 796048 | 6/1958 |
| GB | 883256 A | 11/1961 |
| GB | 930341 A | 7/1963 |
| GB | 950975 | 3/1964 |
| GB | 950976 | 3/1964 |
| GB | 991303 | 5/1965 |
| GB | 995960 | 6/1965 |
| GB | 1015033 | 12/1965 |
| GB | 1104294 | 2/1968 |
| GB | 1133752 | 11/1968 |
| GB | 1172002 | 11/1969 |
| GB | 1212240 | 11/1970 |
| GB | 1233299 | 5/1971 |
| GB | 1253618 | 11/1971 |
| GB | 1263806 | 2/1972 |
| GB | 1446803 | 8/1976 |
| GB | 1542112 | 3/1979 |
| GB | 2095243 A | 9/1982 |
| GB | 2095245 A | 9/1982 |
| GB | 2095249 A | 9/1982 |
| GB | 2116546 A | 9/1982 |
| GB | 2120249 A | 11/1983 |
| GB | 796085 | 6/1985 |
| GB | 2185754 A | 7/1987 |
| GB | 2191214 A | 12/1987 |
| SU | 694483 A1 | 10/1979 |
| WO | 83/00859 | 3/1983 |
| WO | 85/04863 | 11/1985 |
| WO | 85/04867 | 11/1985 |
| WO | 90/08120 | 7/1990 |
| WO | 90/08752 | 8/1990 |
| WO | 91/18856 | 12/1991 |
| WO | 92/03401 | 3/1992 |
| WO | 92/12946 | 8/1992 |
| WO | 93/06039 A1 | 4/1993 |
| WO | 93/16798 | 9/1993 |
| WO | 96/22263 | 7/1996 |
| WO | 97/44302 | 11/1997 |
| WO | 98/12165 | 3/1998 |
| WO | 99/07443 | 2/1999 |
| WO | 00/07718 A1 | 2/2000 |
| WO | 00/09261 A1 | 2/2000 |
| WO | 01/14300 A1 | 3/2001 |
| WO | 01/38275 A1 | 5/2001 |
| WO | 01/44149 A1 | 6/2001 |
| WO | 02/094749 A1 | 11/2002 |
| WO | 02/094750 A1 | 11/2002 |
| WO | 02/094751 A2 | 11/2002 |
| WO | 02/094752 A1 | 11/2002 |
| WO | 03/000635 A1 | 1/2003 |
| WO | 03/002251 A2 | 1/2003 |
| WO | 03/018524 A1 | 3/2003 |
| WO | 03/020676 A1 | 3/2003 |
| WO | 03/022827 A1 | 3/2003 |
| WO | 03/043575 A2 | 5/2003 |
| WO | 03/051813 A1 | 6/2003 |
| WO | 03/062143 A1 | 7/2003 |
| WO | 03/062172 A2 | 7/2003 |
| WO | 03/078366 A1 | 9/2003 |
| WO | 2004/018093 A2 | 3/2004 |
| WO | 2004/067487 A2 | 8/2004 |
| WO | 2005/014168 A1 | 2/2005 |
| WO | 2005/019143 A1 | 3/2005 |
| WO | 2005/021468 A1 | 3/2005 |
| WO | 2005/035121 A2 | 4/2005 |
| WO | 2005/037758 A1 | 4/2005 |
| WO | 2005/054120 A2 | 6/2005 |
| WO | 2005/056525 A2 | 6/2005 |
| WO | 2005/058782 A1 | 6/2005 |
| WO | 2005/090272 A1 | 9/2005 |
| WO | 2005/095310 A2 | 10/2005 |
| WO | 2005/104689 A2 | 11/2005 |
| WO | 2005/105709 A1 | 11/2005 |
| WO | 2005/105715 A1 | 11/2005 |
| WO | 2005/110953 A1 | 11/2005 |
| WO | 2005/113437 A1 | 12/2005 |
| WO | 2005/113440 A1 | 12/2005 |
| WO | 2006/007093 A1 | 1/2006 |
| WO | 2006/015824 A1 | 2/2006 |
| WO | 2006/019399 A2 | 2/2006 |
| WO | 2006/020234 A1 | 2/2006 |
| WO | 2006/036293 A1 | 4/2006 |
| WO | 2006/039213 A1 | 4/2006 |
| WO | 2006/039354 A2 | 4/2006 |
| WO | 2006/043075 A1 | 4/2006 |
| WO | 2006/053345 A1 | 5/2006 |
| WO | 2006/067155 A2 | 6/2006 |
| WO | 2006/067188 A1 | 6/2006 |
| WO | 2006/067190 A1 | 6/2006 |
| WO | 2006/067191 A1 | 6/2006 |
| WO | 2006/067192 A1 | 6/2006 |
| WO | 2006/067193 A1 | 6/2006 |
| WO | 2006/069107 A2 | 6/2006 |
| WO | 2006/071354 A1 | 7/2006 |
| WO | 2006/083427 A2 | 8/2006 |
| WO | 2006/100312 A1 | 9/2006 |
| WO | 2006/104909 A2 | 10/2006 |
| WO | 2006/104914 A1 | 10/2006 |
| WO | 2006/111997 A1 | 10/2006 |
| WO | 2006/113205 A2 | 10/2006 |
| WO | 2006/118935 A2 | 11/2006 |
| WO | 2007/001934 A2 | 1/2007 |
| WO | 2007/017900 A2 | 2/2007 |
| WO | 2007/044139 A1 | 4/2007 |
| WO | 2007/046986 A2 | 4/2007 |
| WO | 2007/050745 A1 | 5/2007 |
| WO | 2007/071046 A1 | 6/2007 |
| WO | 2007/079038 A2 | 7/2007 |
| WO | 2007/091009 A2 | 8/2007 |
| WO | 2007/094995 A2 | 8/2007 |
| WO | 2007/107031 A1 | 9/2007 |
| WO | 2007/111997 A2 | 10/2007 |
| WO | 2007/114479 A1 | 10/2007 |
| WO | 2007/125332 A1 | 11/2007 |
| WO | 2007/130054 A1 | 11/2007 |
| WO | 2007/130055 A1 | 11/2007 |
| WO | 2007/141295 A1 | 12/2007 |
| WO | 2007/142745 A1 | 12/2007 |
| WO | 2008/036562 A1 | 3/2008 |
| WO | 2008/036563 A2 | 3/2008 |
| WO | 2008/106318 A1 | 9/2008 |
| WO | 2008/106319 A1 | 9/2008 |
| WO | 2008/157043 A1 | 12/2008 |
| WO | 2008/157044 A1 | 12/2008 |
| WO | 2008/157045 A1 | 12/2008 |
| WO | 2008/157046 A1 | 12/2008 |
| WO | 2008/157047 A1 | 12/2008 |
| WO | 2009/152403 A1 | 12/2009 |
| WO | 2009/152405 A1 | 12/2009 |
| WO | 2009/152408 A1 | 12/2009 |

(56) References Cited

FOREIGN PATENT DOCUMENTS

| WO | 2010/009376 A1 | 1/2010 |
|---|---|---|
| WO | 2011/008573 A1 | 1/2011 |
| WO | 2011/159490 A1 | 12/2011 |

OTHER PUBLICATIONS

Jacobson, C.A.; "Encyclopedia of Chemical Reactions"; vol. 1, 1946, pp. 722.
U.S. Office Communication from U.S. Appl. No. 12/792,335, dated Aug. 17, 2012.
U.S. Office Communication from U.S. Appl. No. 12/957,036 dated Aug. 16, 2012.
U.S. Office Communication from U.S. Appl. No. 13/157,584 dated May 11, 2012.
U.S. Office Communication from U.S. Appl. No. 13/157,584 dated Aug. 29, 2012.
U.S. Office Communication from U.S. Appl. No. 12/792,335 dated Jan. 2, 2013.
U.S. Office Communication from U.S. Appl. No. 13/053,540 dated Aug. 6, 2013.
U.S. Office Communication from U.S. Appl. No. 13/117,785 dated Mar. 14, 2013.
U.S. Office Communication from U.S. Appl. No. 13/117,785 dated Apr. 22, 2013.
U.S. Office Communication from U.S. Appl. No. 13/212,291 dated May 10, 2013.
U.S. Office Communication from U.S. Appl. No. 13/269,683 dated Jun. 6, 2013.
Abstract of JP Publication No. 08-283182, Production of Hydrochloromethanes, Published Oct. 29, 1996, Inventor: Kojiro et al., http://www19.ipdl.inpit.go.jp . . .
Abstract of WO 96/00696, Method and Apparatus for Recovering Bromine from a Liquid Effluent, Published Jan. 11, 1996, Inventor: Mulet, Jean-Charles et al.
Jackisch; "Bromine" in Kirk-Othmer Encyclopedia of Chemical Technology, 4th Edition, vol. 4, pp. 536-537, 548-550, 560, Published 1992, John Wiley & Sons, Inc. USA.
Kesner, Miri; "How is Bromine Produced" in Bromine Compounds from the Dead Sea, Israel Products in the Service of People; pp. 3, 5, 78, 87; First published in Hebrew in Israel in 1999 by the Department of Science Teaching; The Weizmann Institute of Science.
Mills, "Bromine" Ullmann's Encyclopedia of Industrial Chemistry, Fifth, Completely Revised Edition, vol. A4, pp. 391 and 397, Published 1985, VCH Verlagsgesellschaft mbH, Federal Republic of Germany.
U.S. Appl. No. 60/487,364, filed Jul. 15, 2003, Lorkovic et al.
U.S. Appl. No. 60/559,844, filed Apr. 6, 2004, Sherman et al.
U.S. Appl. No. 60/765,115, filed Feb. 3, 2006, Gadewar et al.
U.S. Office Communication from U.S. Appl. No. 10/365,346 dated Jun. 12, 2006.
U.S. Office Communication from U.S. Appl. No. 10/826,885 dated Oct. 31, 2005.
U.S. Office Communication from U.S. Appl. No. 10/826,885 dated Apr. 19, 2006.
U.S. Office Communication from U.S. Appl. No. 10/826,885 dated Jul. 27, 2006.
U.S. Office Communication from U.S. Appl. No. 10/826,885 dated Nov. 2, 2006.
U.S. Office Communication from U.S. Appl. No. 10/826,885 dated Jan. 24, 2007.
U.S. Office Communication from U.S. Appl. No. 10/893,418 dated Jun. 14, 2007.
U.S. Office Communication from U.S. Appl. No. 10/893,418 dated Jan. 2, 2008.
U.S. Office Communication from U.S. Appl. No. 11/091,130 dated Oct. 3, 2007.
U.S. Office Communication from U.S. Appl. No. 11/101,886 dated Jan. 24, 2007.
U.S. Office Communication from U.S. Appl. No. 11/254,438 dated Jan. 24, 2007.
U.S. Office Communication from U.S. Appl. No. 11/254,438 dated Nov. 1, 2007.
U.S. Office Communication from U.S. Appl. No. 11/778,479 dated Feb. 22, 2010.
U.S. Office Communication from U.S. Appl. No. 12/112,926 dated Jan. 16, 2009.
U.S. Office Communication from U.S. Appl. No. 12/112,926 dated Sep. 14, 2009.
U.S. Office Communication from U.S. Appl. No. 12/112,926 dated Jan. 7, 2010.
U.S. Office Communication from U.S. Appl. No. 12/112,926 dated Jul. 22, 2010.
U.S. Office Communication from U.S. Appl. No. 12/112,926 dated Jan. 7, 2011.
U.S. Office Communication from U.S. Appl. No. 12/123,924 dated Mar. 19, 2010.
U.S. Office Communication from U.S. Appl. No. 12/123,924 dated Aug. 30, 2010.
U.S. Office Communication from U.S. Appl. No. 12/139,135 dated Nov. 24, 2010.
U.S. Office Communication from U.S. Appl. No. 12/502,024 dated Oct. 26, 2010.
U.S. Office Communication from U.S. Appl. No. 12/715,526 dated Feb. 17, 2011.
U.S. Office Communication from U.S. Appl. No. 12/139,135 dated Apr. 14, 2011.
U.S. Office Communication from U.S. Appl. No. 12/715,526 dated May 24, 2011.
U.S. Office Communication from U.S. Appl. No. 12/502,024 dated May 31, 2011.
U.S. Office Communication from U.S. Appl. No. 12/139,135 dated Oct. 14, 2011.
U.S. Office Communication from U.S. Appl. No. 12/477,307 dated Oct. 7, 2011.
U.S. Office Communication from U.S. Appl. No. 12/477,319 dated Jul. 22, 2011.
U.S. Office Communication from U.S. Appl. No. 12/502,024 dated Sep. 16, 2011.
U.S. Office Communication from U.S. Appl. No. 12/477,307 dated Feb. 27, 2012.
U.S. Office Communication from U.S. Appl. No. 12/715,526 dated Jan. 4, 2012.
Abstract of BE 812868, Aromatic hydrocarbons prodn. from chlorinated hydrocarbons, Publication date: Sep. 27, 1974, esp@cenet database—worldwide.
Abstract of BE 814900, Volatile aramatic cpds. prodn., Publication date: Sep. 2, 1974, esp@cenet database—worldwide.
Abstract of BR 0210054, Oxidative halogenation of C1 hydrocarbons to halogenated C1 hydrocarbons and integrated processes related thereto, Publication date: Aug. 17, 2004, Inventor: Schweizer et al., esp@cenet database—worldwide.
Abstract of CA 2447761 A1, Oxidative halogenation of C1 hydrocarbons to halogenated C1 hydrocarbons and integrated processes related thereto, Publication date: Nov. 28, 2002, Inventor: Hickman, et al.
Abstract of CA 2471295 A1, Integrated process for synthesizing alcohols, ethers, and olefins from alkanes, Publication date: Jul. 31, 2003, Inventor: Sherman et al.
Abstract of CN 1199039, Pentanol and its production process, Publication date: Nov. 18, 1998, Inventor: Kailun, esp@cenet database—worldwide.
Abstract of CN 1210847, Process for producing low carbon alcohol by directly hydrating low carbon olefines, Publication date: Mar. 17, 1999, Inventor: Zhenguo et al., esp@cenet database—worldwide.
Abstract of CN 1321728, Method for preparing aromatic hydrocarbon and hydrogen gas by using law-pressure gas, Publication date: Nov. 14, 2001, Inventor: Jie et al., esp@cenet database—worldwide.
Abstract of CN 1451721, Process for non-catalytic combustion deoxidizing coal mine gas for producing methanol, Publication date: Oct. 29, 2003, Inventor: Pengwan et al., esp@cenet database—worldwide.

(56) References Cited

OTHER PUBLICATIONS

Abstract of CN 1623969, Method for preparing 1, 4-benzene dimethanol, Publication date: Jun. 8, 2005, Inventor: Jiarong et al., esp@cenet database—worldwide.
Abstract of CN 1657592, Method for converting oil to multiple energy fuel product, Publication date: Aug. 24, 2005, Inventor: Li, esp@cenet database—worldwide.
Abstract of CN 1687316, Method for producing biologic diesel oil from rosin, Publication date: Oct. 26, 2005, Inventor: Jianchun et al., esp@cenet database—worldwide.
Abstract of CN 1696248, Method for synthesizing biologic diesel oil based on ion liquid, Publication date: Nov. 16, 2005, Inventor: Sun, esp@cenet database—worldwide.
Abstract of CN 1699516, Process for preparing bio-diesel-oil by using miroalgae fat, Publication date: Nov. 23, 2005, Inventor: Miao, esp@cenet database—worldwide.
Abstract of CN 1704392, Process for producing alkylbenzene, Publication date: Dec. 7, 2005, Inventor: Gao, esp@cenet database—worldwide.
Abstract of CN 1724612, Biological diesel oil catalyst and method of synthesizing biological diesel oil using sai catalyst, Publication date: Jan. 25, 2006, Inventor: Gu, esp@cenet database—worldwide.
Abstract of CN 1986737, Process for producing biodiesel oil with catering waste oil, Publication date: Jun. 27, 2007, Inventor: Chen, esp@cenet database—worldwide.
Abstract of CN 100999680, Esterification reaction tech. of preparing biodiesel by waste oil, Publication date: Jul. 18, 2007, Inventor: Weiming, esp@cenet database—worldwide.
Abstract of CN 101016229, Refining method for bromomeoamyl alcohol, Publication date: Aug. 15, 2007, Inventor: Tian, esp@cenet database—worldwide.
Abstract of DE 3209964, Process for the preparation of chlorinated hydrocarbons, Publication date: Nov. 11, 1982, Inventor: Pyke et al., esp@cenet database—worldwide.
Abstract of DE 3210196, Process for the preparation of a monochlorinated olefin, Publication date: Jan. 5, 1983, Inventor: Pyke et al., esp@cenet database—worldwide.
Abstract of DE 3226028, Process for the preparation of monochlorinated olefin, Publication date: Feb. 3, 1983, Inventor: Pyke et al., esp@cenet database—worldwide.
Abstract of DE 3334225, Process for the preparation of 1,2-dichloroethane, Publication date: Apr. 4, 1985, Inventor: Hebgen et al., esp@cenet database—worldwide.
Abstract of DE 4232056, 2,5-Di:methyl-hexane-2,5-di:ol continuous prodn. from tert. butanol—by oxidative dimerisation in two phase system with vigorous stirring, using aq. phase with specified density to facilitate phase sepn., Publication date: Mar. 31, 1994, Inventor: Gnann et al., esp@cenet database—worldwide.
Abstract of DE 4434823, Continuous prodn. of hydroxy-benzyl alkyl ether, Publication date: Apr. 4, 1996, Inventor: Stein et al., esp@cenet database—worldwide.
Abstract of EP 0021497 (A1),Synthesis of polyoxyalkylene glycol monoalkyl ethers., Publication date: Jan. 7, 1981, Inventor: Gibson, esp@cenet database—worldwide.
Abstract of EP 0039471, Process for the preparation of 2-chloro-1,1,1,2,3,3,3-heptafluoropropane., Publication date: Nov. 11, 1981, Inventor: Von Halasz, esp@cenet database—worldwide.
Abstract of EP 0101337, Process for the production of methylene chloride., Publication date: Feb. 22, 1984, Inventor: Olah et al., esp@cenet database—worldwide.
Abstract of EP 0235110, Process for the stabilization of silicalite catalysts., Publication date: Sep. 2, 1987, Inventor: Debras et al., esp@cenet database—worldwide.
Abstract of EP 0407989, Method for the production of 1,1,1-trifluoro-2,2-dichloroethane by photochlorination., Publication date: Jan. 16, 1991, Inventor: Cremer et al., esp@cenet database—worldwide.
Abstract of EP 0442258, Process for the preparation of a polyunsaturated olefin., Publication date: Aug. 21, 1991, Inventor: Gaudin et al., esp@cenet database, worldwide.
Abstract of EP 0465294, Process for the preparation of unsaturated bromides., Publication date: Jan. 8, 1992, Inventor: Decaudin et al., esp@cenet database—worldwide.
Abstract of EP 0549387, Synthesis of n-perfluorooctylbromide., Publication date: Jun. 30, 1993, Inventor: Drivon et al., esp@cenet database—worldwide.
Abstract of EP 0850906, Process and apparatus for the etherification of olefinic hydrocarbon feedstocks, Publication date: Jul. 1, 1998, Inventor: Masson, esp@cenet database—worldwide.
Abstract of EP 0858987, Process for conversion of lighter alkanes to higher hydrocarbons, Publication date: Aug. 19, 1998, Inventor: Amariglio, et al., esp@cenet database—worldwide.
Abstract of EP 1395536, Oxidative halogenation of C1 hydrocarbons to halogenated C1 hydrocarbons and integrated processes related thereto, Publication date: Mar. 10, 2004, Inventor: Schweizer et al., esp@cenet database—worldwide.
Abstract of EP 1404636, Integrated process for synthesizing alcohols and ethers from alkanes, Publication date: Apr. 7, 2004, Inventor: Zhou et al., esp@cenet database—worldwide.
Abstract of EP 1435349 A2, Integrated process for synthesizing alcohols and ethers from alkanes, Publication date: Jul. 7, 2004, Inventor: Zhou et al.
Abstract of EP 1474371, Integrated process for synthesizing alcohols, ethers, and olefins from alkanes, Publication date: Nov. 10, 2004, Inventor: Zhou et al., esp@cenet database—worldwide.
Abstract of FR 2692259, Aromatisation of 2-4C hydrocarbons—using a fixed-mobile-catalytic bed process, Publication date: Dec. 17, 1993, Inventor: Alario et al., esp@cenet database—worldwide.
Abstract of FR 2880019, Manufacturing 1,2-dichloroethane, comprises cracking core hydrocarbonated source, separating into fractions, sending into chlorination reaction chamber and oxychlorination reaction chamber and separating from chambers, Publication date: Jun. 30, 2006, Inventor: Strebelle et al., esp@cenet database—worldwide.
Abstract of FR 2883870, Formation of 1,2-dichloroethane useful in manufacture of vinyl chloride involves subjecting mixture of cracking products obtained by cracking of hydrocarbon source, to a succession of aqueous quenching, alkaline washing, and oxidation steps, Publication date: Oct. 6, 2006, Inventor: Balthasart et al., esp@cenet database—worldwide.
Abstract of FR 2883871, Preparing 1,2-dichloroethane comprises cracking hydrocarbon to form mixture, sending mixture into storage reservoir, supplying mixture into chlorination and/or oxychloration reactor, and separating 1,2-dichloroethane from reactor, Publication date: Oct. 6, 2006, Inventor: Balthasart et al., esp@cenet database—worldwide.
Abstract of IT 1255246, Process for the preparation of dinitrodiphenylmethanes, Publication date: Oct. 20, 1995, Applicant: Enichem Spa et al., esp@cenet database—worldwide.
Abstract of IT 1255358, Process for the synthesis of 1,4-butanediol, Publication date: Oct. 31, 1995, Inventor: Ricci Marco, esp@cenet database—worldwide.
Abstract of JP 2142740, Production of fluoroalcohol, Publication date: May 31, 1990, Inventor: Tsutomu et al., esp@cenet database—worldwide.
Abstract of JP 2144150, Chemical process and catalyst used therefore, Publication date: Jun. 1, 1990, Inventor: Deidamusu et al., esp@cenet database—worldwide.
Abstract of JP 4305542, Production of halogenated hydrocarbon compounds, Publication date: Oct. 28, 1992, Inventor: Shinsuke et al., esp@cenet database—worldwide.
Abstract of JP 6172225, Method for fluorinating halogenated hydrocarbon, Publication date: Jun. 21, 1994, Inventor: Takashi et al., esp@cenet database—worldwide.
Abstract of JP 6206834, Production of Tetrachloroethanes, Publication date: Jul. 26, 1994, Inventor: Toshiro et al., esp@cenet database—worldwide.
Abstract of JP 8266888, Method for decomposing aromatic halogen compound, Publication date: Oct. 15, 1996, Inventor: Yuuji et al., esp@cenet database—worldwide.
Abstract of JP 2001031605, Production of 3-hydroxy-1-cycloalkene, Publication date: Feb. 6, 2001, Inventor: Hideo et al., esp@cenet database—worldwide.

(56) References Cited

OTHER PUBLICATIONS

Abstract of JP 2004-529189 (best available copy).
Abstract of JP 2004075683, Method for producing optically active halogenohydroxypropyl compound and glycidyl compound, Publication date: Mar. 11, 2004, Inventor: Keisuke et al., esp@cenet database—worldwide.
Abstract of JP 2004189655, Method for fluorinating with microwave, Publication date: Jul. 8, 2004, Inventor: Masaharu et al., esp@cenet database—worldwide.
Abstract of JP 2005075798, Method for producing adamantyl ester compound, Publication date: Mar. 24, 2005, Inventor: Norihiro et al., esp@cenet database—worldwide.
Abstract of JP 2005082563, Method for producing 1,3-adamantanediol, Publication date: Mar. 31, 2005, Inventor: Norihiro et al., esp@cenet database—worldwide.
Abstract of JP 2005145977, Process for catalytically oxidizing olefin and cycloolefin for the purpose of forming enol, olefin ketone, and epoxide, Publication date: Jun. 9, 2005, Inventor: Cancheng et al., esp@cenet database—worldwide.
Abstract of JP 2005254092, Method of manufacturing alkynes, Publication date: Sep. 22, 2005, Inventor: Shirakawa Eiji, esp@cenet database—worldwide.
Abstract of JP 2006151892, Preparation method of alcohol derivative, Publication date: Jun. 15, 2006, Inventor: Baba Akio et al., esp@cenet database—worldwide.
Abstract of JP 2006152263, Organic-inorganic hybrid-type mesoporous material, method for producing the same, and solid catalyst, Publication date: Jun. 15, 2006, Inventor: Junko et al., esp@cenet database—worldwide.
Abstract of JP 2006193473, Aryl polyadamantane derivative having carboxy or acid anhydride group and method for producing the same, Publication date: Jul. 27, 2006, Inventor: Yasuto et al, esp@cenet database—worldwide.
Abstract of JP 2006231318, Phosphorus containing macromolecule immobilizing palladium catalyst and method for using the same, Publication date: Sep. 7, 2006, Inventor: Osamu et al., esp@cenet database—worldwide.
Abstract of JP 2006263567, Optical resolution method of optical isomer and optical resolution device, Publication date: Oct. 5, 2006, Inventor: Yoshikazu et al., esp@cenet database—worldwide.
Abstract of JP 2006265157, Method for catalytically activating silicated nucleating agent using phosphazene base, Publication date: Oct. 5, 2006, Inventor: Yoshinori et al., esp@cenet database—worldwide.
Abstract of JP 2006306758, Method for producing biaryl compound, Publication date: Nov. 9, 2006, Inventor: Yuji et al., esp@cenet database—worldwide.
Abstract of JP 2007001942, Production method of para-xylene, Publication date: Jan. 11, 2007, Inventor: Kazuyoshi, esp@cenet database—worldwide.
Abstract of JP 2007015994, Method for synthesizing organic compound in ultra high rate under high temperature and high pressure water, and system of high temperature and high pressure reaction, Publication date: Jan. 25, 2007, Inventor: Hajime et al., esp@cenet database—worldwide.
Abstract of JP 2007045756, Hydrogenation method using diaphragm type hydrogenation catalyst, hydrogenation reaction apparatus and diaphragm type hydrogenation catalyst, Publication date: Feb. 22, 2007, Inventor: Shuji et al., esp@cenet database—worldwide.
Abstract of JP 2007061594, Method for decomposing organohalogen compound and mobile decomposition system, Publication date: Mar. 15, 2007, Inventor: Koichi et al., esp@cenet database—worldwide.
Abstract of JP 2007099729, Method for producing alpha-methylstyrene or cumene, Publication date: Apr. 19, 2007, Inventor: Toshio, esp@cenet database—worldwide.
Abstract of RO 119778, Process for preparing perchloroethylene, Publication date: Mar. 30, 2005, Inventor: Horia et al., esp@cenet database—worldwide.

Abstract of WO 0105737, Method for preparing a carboxylic acid, Publication date: Jan. 25, 2001, Inventor: Pascal et al., esp@cenet database—worldwide.
Abstract of WO 0105738, Method for Preparing a carboxylic acid, Publication date: Jan. 25, 2001, Inventor: Pascal et al., esp@cenet database—worldwide.
Abstract of WO 9721656, Method for making fluoroalkanols, Publication date: Jun. 19, 1997, Inventor: Gillet, esp@cenet database—worldwide.
Abstract of WO 9950213, Method for producing dialkyl ethers, Publication date: Oct. 7, 1999, Inventor: Falkowski et al., esp@cenet database—worldwide.
Abstract of WO 2004092099, Method for producing cyclic enols, Publication date: Oct. 28, 2004, Inventor: Friedrich Marko et al., esp@cenet database—worldwide.
Abstract of WO 2006063852, Electroluminescent polymers and use thereof, Publication date: Jun. 22, 2006, Inventor: Buesing Arne et al., esp@cenet database—worldwide.
Abstract of WO 2006076942, Method for the production of synthetic fuels from oxygenates, Publication date: Jul. 27, 2006, Inventor: Rothaemel et al., esp@cenet database—worldwide.
Abstract of WO 2006136135, Method for decarboxylating C-C cross-linking of carboxylic acids with carbon electrophiles, Publication date: Dec. 28, 2006, Inventor: Goossen Lukas et al., esp@cenet database—worldwide.
Abstract of WO 2007028761, Method for chlorinating alcohols, Publication date: Mar. 15, 2007, Inventor: Rohde et al., esp@cenet database—worldwide.
Abstract of WO 2007128842, Catalytic transalkylation of dialkyl benzenes, Publication date: Nov. 15, 2007, Inventor: Goncalvesalmeida et al., esp@cenet database—worldwide.
Abstract of WO 2007137566, Method for catalytic conversion of organic oxygenated compounds from biomaterials, Publication date: Dec. 6, 2007, Inventor: Reschetilowski, esp@cenet database—worldwide.
Adachi et al., Synthesis of sialyl lewis X ganglioside analogs containing a variable length spacer between the sugar and lipophilic moieties, J. Carbohydrate Chemistry, vol. 17, No. 4-5, 1998, pp. 595-607, XP009081720.
Akhrem et al., Ionic Bromination of Ethane and other alkanes (cycloalkanes) with bromine catalyzed by the polyhalomethane-$2AlBr_3$ aprotic organic superacids under mild conditions, Tetrahedron Letters, vol. 36, No. 51, 1995, pp. 9365-9368, Pergamon, Great Britain.
Bagno et al., Superacid-catalyzed carbonylation of methane, methyl halides, methyl alcohol, and dimethyl ether to methyl acetate and acetic acid, J. Org. Chem. 1990, 55, pp. 4284-4289, Loker Hydrocarbon Research Institute; University of Southern California.
Bakker et al., An exploratory study of the addition reactions of ethyleneglycol, 2-chloroethanol and 1,3-dichloro-2-propanol to 1-dodecene, J. Am. Oil Chem. Soc., vol. 44, No. 9, 1967, pp. 517-521, XP009081570.
Benizri et al., Study of the liquid-vapor equilibrium in the bromine-hydrobromic acid-water system, Hydrogen Energy Vector, 1980, pp. 101-116.
Bouzide et al., Highly selective silver (I) oxide mediated monoprotection of symmetrical diols, Tetrahedron Letters, Elsevier, vol. 38, No. 34, 1997, pp. 5945-5948, XP004094157.
Bradshaw et al., Production of hydrobromic acid from bromine and methane for hydrogen production, Proceedings of the 2001 DOE Hydrogen Program Review, NREL/CP-570-30535, 2001, pp. 1-8.
Chang et al., The conversion of methanol and other O-compounds to hydrocarbons over zeolite catalysts, Journal of Catalysis 47, 1977, Academic Press, Inc., pp. 249-259.
Claude et al., Monomethyl-branching of long n-alkanes in the range from decane to tetracosane on Pt/H-ZSM-22 bifunctional catalyst, Journal of Catalysis 190, 2000, pp. 39-48.
Combined International Search Report and Written Opinion dated Apr. 17, 2007 for PCT/US2006/013394, Applicant: GRT, Inc. , pp. 1-13.
Driscoll, Direct methane conversion, Federal Energy Technology Center, U.S. Department of Energy, M970779, pp. 1-10.

(56) References Cited

OTHER PUBLICATIONS

Fenelonov, et al., Changes in texture and catalytic activity of nanocrystalline MgO during its transformation to MgCl2 in the reaction with 1-chlorobutane, J. Phys. Chem. B 2001, 105, 2001 American Chemical Society, pp. 3937-3941.

Final Report, Abstract, http://chemelab.ucsd.edu/methanol/memos/final.html, May 9, 2004, pp. 1-7.

Gibson, Phase-transfer synthesis of monoalkyl ethers of oligoethylene glycols, J. Org. Chem. 1980, vol. 45, No. 6, pp. 1095-1098, XP002427776.

http://webbook.nist.gov/, Welcome to the NIST chemistry webbook, Sep. 10, 2007, U.S. Secretary of Commerce on Behalf of the United States of America, pp. 1-2.

Ione, et al., Syntheses of hydrocarbons from compounds containing one carbon atom using bifunctional zeolite catalysts, Solid Fuel Chemistry, Khimiya Tverdogo Topliva, 1982, Allerton Press, Inc., vol. 16, No. 6, pp. 29-43.

Jaumain et al., Direct catalytic conversion of chloromethane to higher hydrocarbons over various protonic and cationic zeolite catalysts as studied by in-situ FTIR and catalytic testing, Studies in Surface Science and Catalysis 130, Elsevier Science B.V., 2000, pp. 1607-1612.

JLM Technology Ltd., The Miller GLS Technology for conversation of light hydrocarbons to alcohols, New Science for the Benefit of Humanity, May 31, 2000; pp. 1-10.

Kirk-Othmer, Encyclopedia of Chemical Technology, 4th Edition, vol. 1, A Wiley-Interscience Publication, John Wiley & Sons, 1991, pp. 946-997.

Liu et al., Higher hydrocarbons from methane condensation mediated by HBr, Journal of Molecular Catalysis A: Chemical 273, Elsevier B.V., 2007, pp. 14-20.

Loiseau et al., Multigram synthesis of well-defined extended bifunctional polyethylene glycol (PEG) chains, J. Org. Chem., vol. 69, No. 3, XO-002345040, 2004, pp. 639-647.

Lorkovic et al., A novel integrated process for the functionalization of methane and ethane: bromine as mediator, Catalysis Today 98, 2004, pp. 317-322.

Lorkovic et al., C1 oxidative coupling via bromine activation and tandem catalytic condensation and neutralization over CaO/zeolite composites II. Product distribution variation and full bromine confinement, Catalysis Today 98, 2004, pp. 589-594.

Lorkovic et al., C1 coupling via bromine activation and tandem catalytic condensation and neutralization over CaO/ zeolite composites, Chem. Comm. 2004, pp. 566-567.

Mihai, et al., Application of Bronsted-type LFER in the study of the phospholipase C Mechanism, J. Am. Chem. Soc., vol. 125, No. 11, XP-002427777, 2003, pp. 3236-3242.

Mishakov et al., Nanocrystalline MgO as a dehydrohalogenation catalyst, Journal of Catalysis 206, Elsevier Science, USA, 2002, pp. 40-48.

Mochida, et al., The catalytic dehydrohalogenation of haloethanes on solid acids and bases, Bulletin of the Chemical Society of Japan, vol. 44, Dec. 1971, pp. 3305-3310.

Motupally et al., Recycling chlorine from hydrogen chloride, The Electrochemical Society Interface, Fall 1998, pp. 32-36.

Murray et al., Conversion of methyl halides to hydrocarbons on basic zeolites: a discovery by in situ NMR, J. Am. Chem. Soc., 1993, vol. 115, pp. 4732-4741.

Nishikawa et al., Ultrasonic relaxations in aqueous solutions of alcohols and the balance between hydrophobicity and hydrophilicity of the solutes, J. Phys. Chem., vol. 97, No. 14, XP-002427775, 1993, pp. 3539-3544.

Olah et al., Antimony pentafluoride/graphite catalyzed oxidative carbonylation of methyl halides with carbon monoxide and copper oxides (or copper/oxygen) to methyl acetate, J. Org. Chem. 1990, 55, pp. 4293-4297.

Olah et al., Antimony pentafluoride/graphite catalyzed oxidative conversion of methyl halides with copper oxides (or copper/oxygen) to dimethyl ether, J. Org. Chem. 1990, 55, pp. 4289-4293.

Olah, Electrophilic methane conversion, American Chemical Society, Acc. Chem. Res. 1987, 20, pp. 422-428.

Olah, Hydrocarbons through methane derivatives, Hydrocarbon Chemistry, 1995, pp. 89-90, John Wiley & Sons, Inc.

Olah et al., Hydrocarbons through methane derivatives, Hydrocarbon Chemistry, 2nd Edition, 2003, pp. 123, 149, and 153, John Wiley & Sons, Inc.

Olah et al., Onium Ylide Chemistry. 1. Bifunctional acid-base-catalyzed conversion of heterosubstituted methanes into ethylene and derived hydrocarbons. The Onium Ylide mechanism of the C1-C2 conversion. J. Am. Chem. Soc. 1984, 106, pp. 2143-2149.

Olah et al., Selective monohalogenation of methane over supported acid or platinum metal catalysts and hydrolysis of methyl halides over y-alumina-supported metal oxide/hydroxide catalysts. A feasible path for the oxidative conversion of methane into methyl alcohol/dimethyl ether., J. Am. Chem. Soc. 1985, 107, pp. 7097-7105.

Prelog et al., 234. Chirale 2, 2'-polyoxaalkano-9,9'-spirobifluorene, Helvetica Chimica ACTA, vol. 62, No. 7, 1979 pp. 2285-2302.

Rakoff et al., Quimica Organica Fundamental, Organic Chemistry, The Macmillan Company, 1966, pp. 58-63 and 76-77.

Richards, et al., Nanocrystalline ultra high surface area magnesium oxide as a selective base catalyst, Scripta Materialia, 44, 2001, pp. 1663-1666, Elsevier Science Ltd.

Shimizu et al., Gas-Phase electrolysis of hydrobromic acid using PTFE-bonded carbon electrode, Int. J. Hydrogen Energy, vol. 13, No. 6, pp. 345-349, 1988.

Smirnov et al., Selective bromination of alkanes and arylalkanes with CBr4, Mendeleev Commun., 2000, pp. 175-176.

Sun et al., Nanocrystal metal oxide—Chlorine adducts: selective catalysts for chlorination of alkanes, J. Am. Chem. Soc., 1999, 121, pp. 5587-5588.

Sun et al., A general integrated process for synthesizing olefin oxides, Chem. Commun., The Royal Society of Chemistry 2004, pp. 2100-2101.

Tamura et al., The reactions of grignard reagents with transition metal halides: Coupling, disproportionation, and exchange with olefins, Bulletin of the Chemical Society of Japan, vol. 44, Nov. 1971, pp. 3063-3073.

Taylor et al., Direct conversion of methane to liquid hydrocarbons through chlorocarbon intermediates, 1988, Elsevier Science Publishers B.V. Amsterdam, Netherlands, pp. 483-489.

Taylor, Conversion of substituted methanes over ZSM-catalysts, 2000, pp. 3633-3638, Studies in Surface Science and Catalysis 130, Elsevier Science B.V.

Taylor, PETC's on-site neural gas conversion efforts, Preprints of the Fuel Division, 208th National Meeting of the American Chemical Society, 39 (4), 1994, pp. 1228-1232.

Thomas et al., Catalytically active centres in porous oxides: design and performance of highly selective new catalysts, Chem. Commun., 2001, pp. 675-687.

Thomas et al., Synthesis and characterization of a catalytically active nickel-silicoaluminophosphate catalyst for the conversion of methanol to ethene, American Chemical Society, 1991, 3, pp. 667-672.

Van Velzen et al., HBr electrolysis in the Ispra mark 13A flue gas desulphurization process: electrolysis in a DEM cell, Journal of Applied Electrochemistry, 20, 1990, pp. 60-68.

Wagner et al., Reactions of VX, GD, and HD with nanosize CaO: autocatalytic dehydrohalogenation of HD, J. Phys. Chem. B 2000, 104, pp. 5118-5123, 2000 American Chemical Society.

Wauters et al., Electrolytic membrane recovery of bromine from waste hydrogen bromide streams, AIChE Journal, Oct. 1998, vol. 44, No. 10, pp. 2144-2148.

Weissermel et al., Industrial Organic Chemistry, 3rd Edition, 1997, pp. 160-162, and 208.

Whitesides et al., Nuclear magnetic resonance spectroscopy. The effect of structure on magnetic nonequivalence due to molecular asymmetry, J. Am. Chem. Soc., vol. 86, No. 13, 1964, pp. 2628-2634, XP002427774.

Yilmaz et al., Bromine mediated partial oxidation of ethane over nanostructured zirconia supported metal oxide/ bromide, Microporous and Mesoporous Materials, 79, 2005, Science Direct, Elsevier, pp. 205-214.

(56) References Cited

OTHER PUBLICATIONS

Zhou et al., An integrated process for partial oxidation of alkanes, Chem. Commun., 2003, The Royal Society of Chemistry, pp. 2294-2295.

ZSM-5 Catalyst, http://chemelba.ucsd.edu/methanol/memos/ZSM-5.html, Nov. 6, 2003, p. 1.

Abstract of GB 998681(A), Improvements in or relating to the recovery of bromine from bromine-containing materials, Publication date: Jul. 21, 1965, Applicant: Electro Chimie Metal+, espacenet worldwide database.

Abstract of JP 55-073619, Condensation of methyl chloride through dehydrochlorination, Publication date: Jun. 3, 1980, Inventor: Shigeo et al., http://www19.ipdl.inpit.go.jp/PA1/result. . . .

Hannus, Adsorption and transformation of halogenated hydrocarbons over zeolites, Applied Catalysis A: General 189, 1999, XP-002634422, pp. 263-276.

Howe, Zeolite catalysts for dehalogenation processes, Applied Catalysis A: General 271, 2004, XP-002634421, pp. 3-11.

Li et al., Pyrolysis of Halon 1301 over zeolite catalysts, Microporous and Mesoporous Materials 35-36, 2000, XP-002634423, pp. 219-226.

Chretien; Process for the Adjustment of the HHV in the LNG Plants; 23rd World Gas Conference; Amsterdam 2006; Jun. 5-9, 2006; pp. 1-14.

Yang et al.; Maximising the Value of Surplus Ethane and Cost-Effective Design to Handle Rich LNG; publ. date Jun. 1, 2007; pp. 1-13.

U.S. Office Communication from U.S. Appl. No. 13/053,540 dated Jan. 8, 2014.

U.S. Office Communication from U.S. Appl. No. 13/173,847 dated Jan. 21, 2014.

U.S. Office Communication from U.S. Appl. No. 13/679,600 dated Jan. 17, 2014.

U.S. Office Communication from U.S. Appl. No. 13/705,106 dated Feb. 3, 2014.

U.S. Office Communication from U.S. Appl. No. 13/713,926 dated Jan. 30, 2014.

\* cited by examiner

PROCESSES AND SYSTEMS FOR SEPARATE, PARALLEL METHANE AND HIGHER ALKANES' BROMINATION

CROSS-REFERENCE TO RELATED APPLICATIONS

This application claims priority to U.S. Provisional Application No. 61/550,059, filed on Oct. 21, 2011, the disclosure of which is incorporated herein by reference.

BACKGROUND

The present invention relates generally to processes and systems for alkane bromination and, in one or more embodiments, to separate, parallel methane and higher alkanes' bromination in a bromine-based process for converting lower molecular weight alkanes to higher molecular weight hydrocarbons.

Alkyl bromides may be used in the production of a variety of desirable products, including, but not limited to, alcohols, ethers, olefins, and higher hydrocarbons, such as C3, C4, and C5+ gasoline-range and heavier hydrocarbons. For instance, alkyl bromides may be converted to corresponding alcohols over a metal oxide. In another instance, alkyl bromides may be converted to higher molecular weight hydrocarbons over an appropriate catalyst. The term "alkyl bromides," as used herein, refers to mono-, di-, and tri-brominated alkanes, and combinations of these. Poly-brominated alkanes include di-brominated alkanes, tri-brominated alkanes and mixtures thereof.

To produce alkyl bromides, alkanes may be brominated with a source of bromine. In one instance, a gaseous feed comprising lower molecular weight alkanes may be reacted with bromine vapor to form alkyl bromides. It has been observed that of the light alkanes (e.g., C1-C3 alkanes) methane is the least reactive with bromine, whereas ethane is more reactive than methane, and propane and butanes are even more reactive than ethane. Some of the reactions that occur during the bromination of light alkanes are shown below:

   (1)

   (2)

   (3)

   (4)

   (5)

   (6)

   (7)

   (8)

It has further been observed that, for fast conversion of methane to mono-bromomethane, temperatures in excess of 400° C. are typically required. However, if significant quantities of C2+ alkanes (e.g., significantly greater than about 2 mole percent) are present in the bromination feed, these C2+ alkanes become poly-brominated at the high temperatures needed for fast methane conversion. In addition, at these higher temperatures, substantial quantities of soot can be also be formed from the C2+ alkanes, as represented by equations (7) and (8), lowering the carbon efficiency of the process and requiring larger recycle rates of bromine to achieve a given level of methane conversion.

A variety of different attempts have been made to address these problems associated with alkane bromination. In processes for the conversion of alkanes to higher molecular weight hydrocarbons, it has been proposed to separate the C2+ alkanes from the excess methane in the synthesis effluent stream and then react these C2+ alkanes with the di-bromomethane by-product from methane bromination in the vapor phase. Drawbacks to this proposal include a slower than desired reaction rate at temperatures in the range of about 250° C. to about 400° C. whereas at higher temperatures (e.g., above about 450° C.) thermal cracking of propane or reaction products may lead to undesirable soot formation. Alternatively, the heterogeneous reaction of C2+ alkanes with di-bromomethane can be promoted with various catalysts at temperatures below about 400° C., but significant amounts of coke can form with these catalysts resulting in less than desired carbon efficiency.

Thus, there exists a need for processes and systems for alkane bromination that can brominate methane at a desired rate while minimizing the amount of soot formed from C2+ alkanes.

SUMMARY

To achieve the foregoing and other objects, and in accordance with the purposes of the present invention, as embodied and broadly described herein, one embodiment of the present invention is a bromine-based process for converting alkanes to liquid hydrocarbons that includes alkane bromination, the process comprising: brominating a methane stream comprising methane and having less than about 2 mole percent ("mol %") of ethane to form methane bromination products comprising brominated methane and a first fraction of hydrogen bromide; separately brominating a C2+ alkane stream comprising an alkane having 2 or more carbon atoms to form C2+ methane bromination products comprising brominated alkanes having 2 or more carbon atoms and a second fraction of hydrogen bromide; and catalytically reacting at least a portion of the brominated methane and the brominated alkanes to form higher molecular hydrocarbons.

Another embodiment of the present invention is bromine-based process for converting alkanes to liquid hydrocarbons that includes alkane bromination, the process comprising: brominating a methane stream in a bromination reactor to form methane bromination products comprising brominated methane and a first fraction of hydrogen bromide, the methane stream comprising methane and having less than about 1 mol % of ethane and less than about 0.10 mol % of hydrocarbons having 3 or more carbon atoms; separately brominating a C2+ alkane stream in a C2+ bromination reactor to form C2+ methane bromination products comprising brominated alkanes having 2 or more carbon atoms and a second fraction of hydrogen bromide, the C2+ alkane stream comprising ethane, propane, and butane; and catalytically reacting at least a portion of the brominated methane and the brominated alkanes in a synthesis reactor to form higher molecular weight hydrocarbons and a third fraction of hydrogen bromide.

Another embodiment of the present invention is a system for converting alkanes to liquid hydrocarbons comprising: a first bromination reactor configured for bromination of methane to produce a methane bromination product stream comprising brominated methane and a first fraction of hydrogen bromide; a second bromination reactor configured for bromination of C2+ hydrocarbons to produce a C2+ bromination product stream comprising brominated hydrocarbons having 2 or more alkanes and hydrogen bromide; and a synthesis reactor configured for catalytically reacting the brominated methane and brominated hydrocarbons to form higher molecular weight hydrocarbons and a third fraction of hydrogen bromide.

DETAILED DESCRIPTION OF PREFERRED EMBODIMENTS

The present invention relates generally to processes and systems for alkane bromination and, in one or more embodiments, to separate, parallel methane and higher alkanes' bromination in a bromine-based process for converting lower molecular weight alkanes to higher molecular weight hydrocarbons.

There may be many potential advantages to the processes and systems of the present invention, only some of which are alluded to herein. One of the many potential advantages of embodiments of the processes and systems of the present invention is that soot in the bromination reactor can be minimized by separately brominating methane and higher alkanes. Another potential advantage of embodiments of the processes and systems of the present invention is that it has been found that the mono- and poly-brominated C2+ alkanes from the separate bromination should couple efficiently in the synthesis reactor for conversion of alkyl bromides to higher molecular weight hydrocarbons, thus minimizing coke formation in the synthesis reactor. It is surmised that unlike di-bromomethane (which has a hydrogen-to-bromine ratio of 1), the higher alkyl bromides, including even the polybrominated C2+ alkanes, have hydrogen-to-bromine ratios of greater than 2 and thus, upon dehydrohalogenation, are still able to produce reactive alkyl radicals which can couple and oligomerize into higher molecular weight hydrocarbon products, including aromatics. This is illustrated in the following simple example reaction equations for di-bromoethane and di-bromopropane:

$$C_2H_4Br_2 \rightarrow 2HBr + {}^*C_2H_2 \quad (9)$$

$$C_3H_6Br_2 \rightarrow 2HBr + {}^*C_3H_4 \quad (10)$$

It is therefore feasible, and in fact preferable to combine the effluents from the separate methane bromination and higher alkane bromination(s), prior to conversion to higher molecular weight hydrocarbons over a suitable catalyst, such as a synthetic crystalline alumino-silicate catalyst. Accordingly, by minimizing soot formation in the bromination reactor and coke formation in the synthesis reactor, the carbon efficiencies and practical operability the processes and systems can be improved in accordance with embodiments of the present invention.

Figure 1:
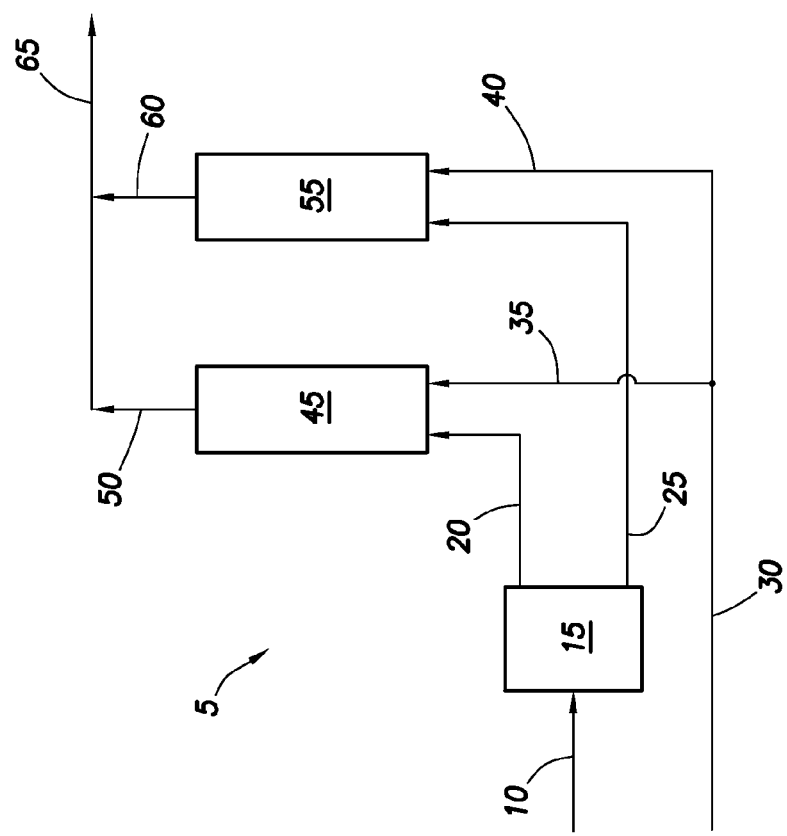
FIG. 1 is a schematic diagram illustrating a bromination process for separate, parallel methane and higher alkanes' bromination in accordance with embodiments of the present invention.

FIG. 1 is a schematic diagram illustrating a bromination process 5 for separate, parallel methane and higher alkanes' bromination in accordance with embodiments of the present invention. In the illustrated embodiment, alkane stream 10 may be fed into alkane separation unit 15. The alkane stream 10 generally comprises a mixture of C1-C3 alkanes, namely methane, ethane, and propane. Alkane stream 10 may also comprise a minor portion (e.g., less than about 25 mol %) of C4+ alkanes, such as butane, for example. The alkane stream 10 may be at a pressure, for example, of about 1 atmosphere ("atm") to about 100 atm or, alternatively, about 1 atm to about 30 atm. While not illustrated, the alkane stream 10 may comprise recycled alkanes that are produced in subsequent process units (not illustrated) and/or make-up alkanes that are introduced into the bromination process 5.

In the alkane separation unit 15, the alkane stream 10 may be separated into a methane stream 20 and a C2+ alkane stream 25. The methane stream 20 and C2+ alkane stream 25 leaving the alkane separation unit 15 may be at a pressure, for example, of about 1 atm to about 100 atm or, alternatively, about 1 atm to about 30 atm. The methane stream 20 may comprise methane, and the C2+ alkane stream 25 may comprise ethane, propane, butane, or mixtures thereof. In some embodiments, the methane stream 20 may also comprise minimal concentrations of C2+ alkanes. For example, the methane stream 20 may comprise ethane in an amount of about 2 mol % or less, preferably, about 1.5 mol % or less, or, alternatively, about 1 mol % or less. By way of further example, the methane stream 20 may comprise C3+ alkanes (e.g., propane, butane, etc.) in an amount of about 0.1 mol % or less, or, alternatively, about 0.05 mol % or less. Any suitable technique for separation of the C2+ alkanes from methane may be used in accordance with embodiments of the present invention. In some embodiments, the separation may achieved by means of cryogenic separation, such as those used in natural gas processing, in a manner as should be evident to those of ordinary skill in the art with the benefit of this disclosure.

As illustrated, a bromine feed stream 30 may be split into a first bromine stream 35 and a second bromine stream 40. The bromine feed stream 30 may be at a pressure, for example, of about 1 atm to about 100 atm or, alternatively, about 1 atm to about 30 atm. In certain embodiments, the bromine present in the bromine feed stream 30 may be in a gaseous state, a liquid state, or a mixture thereof. While not illustrated, in certain embodiments, the bromine feed stream 30 may contain recycled bromine that is recovered in the bromination process 5 and/or make-up bromine that is introduced into the bromination process 5. Suitable sources of bromine that may be used in various embodiments of the present invention include, but are not limited to, elemental bromine, bromine salts, aqueous hydrobromic acid, metal bromide salts, and the like. Combinations may be suitable, but as should be recognized by those skilled in the art with the benefit of this disclosure, using multiple sources may present additional complications. In some embodiments, the bromine in the bromine feed stream 30 may be dry bromine in that the bromine is substantially water-free.

In some embodiments, the methane stream 20 and first bromine stream 35 may be introduced into a C1 bromination reactor 45. While FIG. 1 illustrates separate introduction of the methane stream 20 and first bromine stream 35 into the C1 bromination reactor 45, those of ordinary skill in the art, with the benefit of this disclosure, should appreciate that the streams can combined prior to their introduction into the C1 bromination reactor 45. The methane stream 20 and first bromine stream 35 may be allowed to react to form a C1 bromination product stream 50 that comprises alkyl bromides (e.g., brominated methane, such as mono-bromomethane, di-bromomethane, etc.) hydrogen bromide ("HBr"), and unreacted excess alkanes (e.g., methane, ethane, propane, etc.). The C1 bromination product stream 50 may be withdrawn from the C1 bromination reactor 45.

In the C1 bromination reactor 45, the gaseous methane and any C2+ alkanes in the methane stream 20 may be reacted exothermically with bromine in the first bromine stream 35, for example, at a temperature in the range of about 250° C. to about 600° C., and at a pressure in the range of about 1 atm to about 50 atm to produce gaseous alkyl bromides and HBr. In some embodiments, the temperature may be at about 400° C. or greater. In some embodiments, the temperature may range from about 490° C. to about 570° C. In some embodiments, the pressure may range from about 1 atm to about 30 atm. Residence times may be, for example, from about 5 seconds to about 90 seconds and, alternatively, about 45 seconds to about 60 seconds. The higher temperatures above about 500° C. and residence times of about 60 seconds generally can result in higher selectivities to mono-bromomethane of at least about 90 mol % (e.g., approximately 90 mol %) for the brominated C1 alkanes and hence, lower selectivities to di-bromomethane and tri-bromomethane, which should generally reduce the amount of coke formed in the downstream synthesis reactor. In some embodiments, the feeds to the C1 bromination reactor 45 may be pre-heated to a temperature of about 250° C. to about 490° C., for example, in an inlet pre-heater zone. It should be understood that the upper limit of the operating temperature range is greater than the upper limit of the reaction initiation temperature range to which the feed mixture may be heated due to the exothermic nature of the bromination reaction. Those of ordinary skill in the art should appreciate, with the benefit of this disclosure that the bromination reaction may be a non-catalytic (thermal) or a catalytic reaction in a manner as will be evident to those of ordinary skill in the art.

The methane/bromine molar ratio of the feed introduced to the C1 bromination reactor 45 may be at least about 2.5:1, in some embodiments, and at least about 5:1 in alternative embodiments. In some embodiments, a larger excess of methane (e.g., about 3:1 to about 10:1) may be used in order to achieve desirable selectivity of mono-bromomethane, as mono-bromomethane is more rapidly brominated than methane under free radical conditions. As previously mentioned, the C2+ alkane content in the methane stream 20 may be controlled by separation in the alkane separation unit 15. It has been observed that, by reducing the levels of C2+ alkanes in the feed to the C1 bromination reactor 45, the production of soot can be minimized in accordance with embodiments of the present invention. For example, to reduce soot formation, the propane concentration in the methane stream 20 fed to the C1 bromination reactor 45 may be about 0.1 mol % or less. Because ethane is generally less reactive than propane, higher concentrations can be tolerated while minimizing soot formation, thus the ethane concentration in the methane stream 20 fed to the C1 bromination reactor 45 may be about 2 mol % or less.

In some embodiments, the C2+ alkane stream 25 and second bromine stream 40 may be fed to a C2+ bromination reactor 55. While FIG. 1 illustrates separate introduction of the C2+ alkane stream 25 and second bromine stream 40 into the C2+ bromination reactor 55, those of ordinary skill in the art should appreciate, with the benefit of this disclosure, that the streams can combined prior to their introduction into the C2+ bromination reactor 55. The C2+ alkane stream 25 and second bromine stream 40 may be allowed to react to form a C2+ bromination product stream 60 that comprises alkyl bromides, HBr, and unreacted C2+ alkanes (e.g., ethane, propane, etc.). The alkyl bromides may comprise, for example, brominated ethane, such as mono-bromoethane, di-bromoethane, and tri-bromoethane, brominated propane, such as mono-bromopropane, di-bromopropane, and tri-bromopropane, and brominated butane, such as mono-bromobutane, di-bromobutane, and tri-bromobutane. The C2+ bromination product stream 60 may be withdrawn from the C2+ bromination reactor 55.

In the C2+ bromination reactor 55, the gaseous C2+ alkanes (e.g., ethane, propane, butane, etc.) in the C2+ alkane stream 25 may be reacted exothermically with bromine in the second bromine stream 40, for example, at a temperature in the range of about 250° C. to about 450° C., and at a pressure in the range of about 1 atm to about 50 atm to produce gaseous alkyl bromides and HBr. In some embodiments, the temperature may be in the range of about 300° C. to about 375° C. In some embodiments, the pressure may range from about 1 atm to about 30 atm. Residence times may be, for example, from about 5 seconds to about 60 seconds and, alternatively, about 15 seconds to about 45 seconds. Longer residence times are required for complete conversion of bromine at lower temperatures, however the formation of soot is minimized in the lower temperature ranges. In some embodiments, the feeds to the C2+ bromination reactor 55 may be pre-heated to a temperature of about 250° C. to about 350° C., for example, in an inlet pre-heater zone. It should be understood that the upper limit of the operating temperature range is greater than the upper limit of the reaction initiation temperature range to which the feed mixture may be heated due to the exothermic nature of the bromination reaction. Those of ordinary skill in the art should appreciate, with the benefit of this disclosure that the bromination reaction may be a non-catalytic (thermal) or a catalytic reaction in a manner as will be evident to those of ordinary skill in the art.

It has been observed that C2+ alkanes can be efficiently brominated with a smaller excess of alkanes as compared to that required for methane without excessive soot formation, so the C2+ alkane/bromine molar ratio of the feed introduced to the C2+ bromination reactor 55 may be less than about 2.5:1, in some embodiments. In some embodiments, the C2+ alkane/bromine molar ratio of the feed may be in the range of about 1.33:1 to about 2.5:1 and, preferably about 1.5:1 to about 2.0:1. By maintaining excess alkane in the C2+ bromination reactor 55 at the higher end of the range, the selectivity to mono-brominated alkanes can be increased, yet the formation of soot can be minimized even towards the low end of the range, for example. Even though more poly-brominated alkanes may be formed with lower ratios of alkane to bromine, the poly-brominated C2+ alkanes may not have an undesirable impact on subsequent processing steps. For example, in the reaction of the alkyl bromides over a crystalline alumino-silicate catalyst, such as a zeolite catalyst, to form higher molecular weight alkanes, the poly-brominated C2+ alkanes may not have excess selectively to coke formation on the catalyst, because these C2+ poly-brominated alkanes may still have a hydrogen-to-bromine ratio of greater than 1 and, upon dehydrohalogenation, are still able to form reactive alkyl radicals which can couple and oligomerize into higher molecular weight hydrocarbons, including aromatics, when compared to the selectivity of coke formation of poly-brominated methane which have a hydrogen-to-bromine ratio of less than or equal to 1.

As illustrated, the C1 bromination product stream 50 and C2+ bromination product stream 60 may be combined to form combined bromination product stream 65, which may comprise brominated methane, brominated ethane, brominated propane, and brominated butane, for example. In accordance with present embodiments, the bromination product stream 65 may be routed to subsequent process units (not illustrated). In alternative embodiments (not illustrated), the C1 bromination product stream 50 and the C2+ bromination product stream 60 may be separately routed to subsequent process units without combination. In some embodiments, the alkyl bromides present in the bromination product stream 65 may be reacted over a suitable catalyst to form higher molecular weight hydrocarbons.

Figure 2:
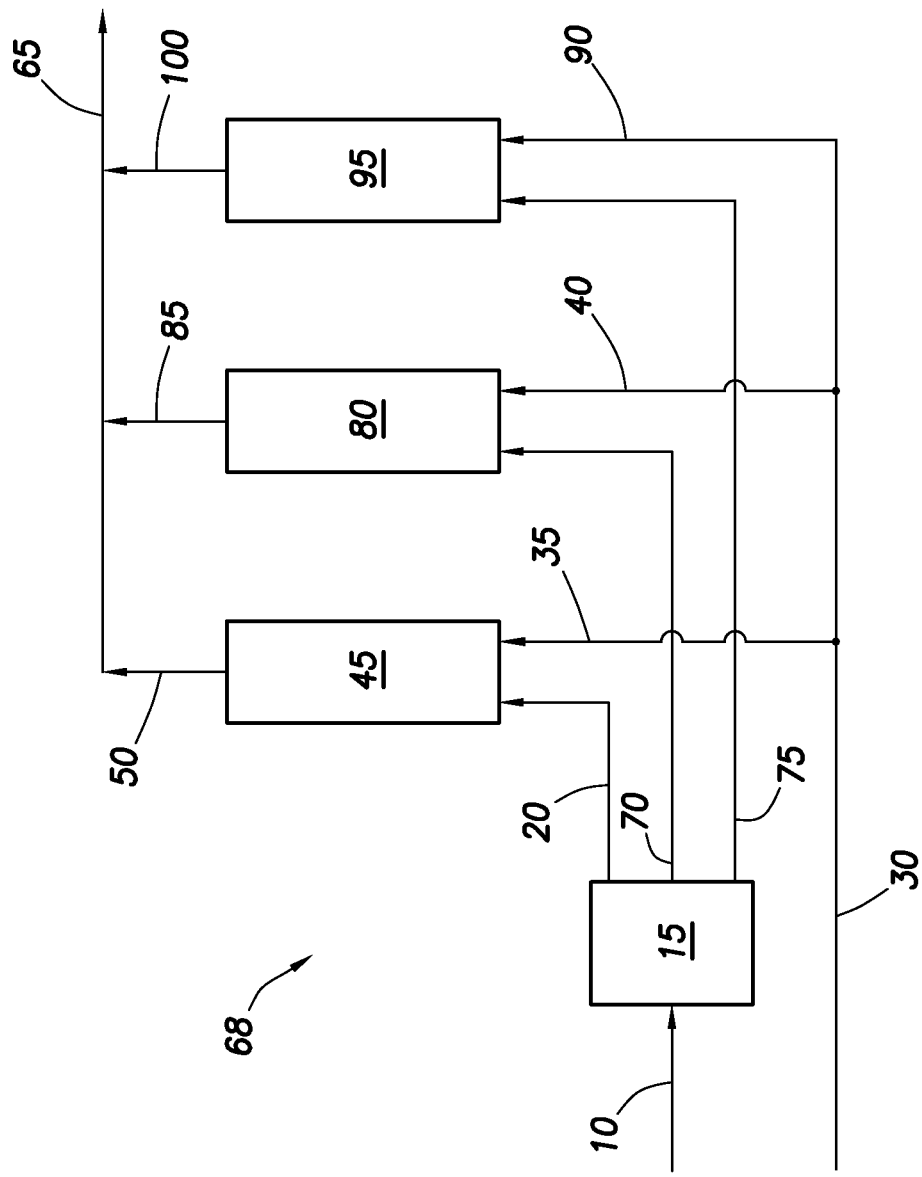
FIG. 2 is a schematic diagram illustrating a second bromination process for separate, parallel methane and higher alkanes' bromination in accordance with alternative embodiments of the present invention.

FIG. 2 is a schematic diagram illustrating a second bromination process 68 for separate, parallel methane and higher alkanes' bromination in accordance with alternative embodiments of the present invention. The illustrated embodiment is similar to the embodiment depicted in FIG. 1 except that the alkane separation unit 15 separates the alkane stream 10 into a methane stream 20, an ethane stream 70, and a C3+ alkane stream 75. The streams leaving the alkane separation unit 15 may be at a pressure, for example, of about 1 atm to about 100 atm or, alternatively, about 1 atm to about 30 atm. The methane stream 20 may comprise methane, the ethane stream 70 may comprise ethane, and the C3+ alkane stream may comprise propane, butane, or mixtures thereof. The concentration specification on the methane stream 20 for ethane and C3+ alkanes may be as described above with respect to FIG. 1. In some embodiments, the ethane stream 70 may comprise C3+ alkanes in an amount of about 10 mol % or less and, alternatively, about 1 mol % or less. It is notable that, due to the reduced reactivity of ethane relative to propane, any ethane present at low concentrations will remain mostly unreacted, and so it may be preferable to separate the ethane from the propane and brominate the ethane and propane separately.

In some embodiments, the methane stream 20 and first bromine stream 35 may be introduced into a C1 bromination reactor 45. The methane stream 20 and first bromine stream 35 may be allowed to react to form a C1 bromination product stream 50 that comprises alkyl bromides, HBr, and unreacted excess methane. The C1 bromination product stream 50 may be withdrawn from the C1 bromination reactor 45.

In some embodiments, the ethane stream 70 and second bromine stream 40 may be fed to a C2 bromination reactor 80. While FIG. 2 illustrates separate introduction of the ethane stream 70 and second bromine stream 40 into the C2 bromination reactor 80, those of ordinary skill in the art should appreciate, with the benefit of this disclosure, that the streams can combined prior to their introduction into the C2 bromination reactor 80. The ethane stream 70 and second bromine stream 40 may be allowed to react to form a C2 bromination product stream 85 that comprises alkyl bromides (e.g., brominated ethane, such as mono-bromoethane, di-bromoethane, and tri-bromoethane), HBr, and unreacted excess ethane. The C2 bromination product stream 85 may be withdrawn from the C2 bromination reactor 80.

In the C2 bromination reactor 80, the gaseous ethane in the ethane stream 70 may be reacted exothermically with bromine in the second bromine stream 40, for example, at a temperature in the range of about 225° C. to about 450° C., and at a pressure in the range of about 1 atm to about 50 atm to produce gaseous alkyl bromides and HBr. In some embodiments, the temperature may be in the range of about 250° C. to about 375° C. Residence times may be, for example, from about 5 seconds to about 60 seconds and alternatively, about 15 seconds to about 45 seconds. Lower temperatures reduce the formation of soot and improve selectivity to mono-bromoethane, however at lower temperatures, longer residence times are required for complete reaction of the bromine. In some embodiments, the feeds to the C2 bromination reactor 80 may be pre-heated to a temperature of about 250° C. to about 350° C., for example, in an inlet pre-heater zone. It should be understood that the upper limit of the operating temperature range is greater than the upper limit of the reaction initiation temperature range to which the feed mixture may be heated due to the exothermic nature of the bromination reaction. Those of ordinary skill in the art should appreciate, with the benefit of this disclosure that the bromination reaction may be a non-catalytic (thermal) or a catalytic reaction in a manner as will be evident to those of ordinary skill in the art.

It has been observed that the ethane can also be efficiently brominated without as large an excess of alkane as is required in the case of methane bromination so the ethane/bromine molar ratio of the feed introduced to the C2 bromination reactor 80 may be less than about 2.5:1, in some embodiments. In some embodiments, the ethane/bromine molar ratio of the feed may be in the range of about 1.33:1 to about 2.5:1 and, preferably about 1.5:1 to about 2.0:1. By maintaining excess ethane in the C2 bromination reactor 80 at the higher end of the range, the selectivity to mono-brominated ethane can be increased, yet the formation of soot can be minimized. Even though more poly-brominated ethane may be formed with lower ratios of alkane to bromine, the poly-brominated ethane may not have an undesirable impact on subsequent processing steps. For example, in the reaction of the alkyl bromides over a crystalline alumino-silicate catalyst, such as a zeolite catalyst, to form higher molecular weight alkanes, the poly-brominated C2+ alkanes may not have excess selectively to coke formation on the catalyst, when compared to the selectivity of coke formation of poly-brominated methane.

In some embodiments, the C3+ alkane stream 75 and a third bromine stream 90 may be fed to a C3+ bromination reactor 95. While FIG. 2 illustrates separate introduction of the C3+ alkane stream 75 and third bromine stream 90 into the C3+ bromination reactor 95, those of ordinary skill in the art should appreciate, with the benefit of this disclosure, that the streams can combined prior to their introduction into the C3+ bromination reactor 95. The C3+ alkane stream 75 and third bromine stream 90 may be allowed to react to form a C3+ bromination product stream 100 that comprises alkyl bromides, HBr, and unreacted C3+ alkanes. The alkyl bromides may include, for example, brominated propane (e.g., mono-bromopropane, di-bromopropane, and tri-bromopropane)

and brominated butane (e.g., mono-bromobutane, di-bromobutane, tri-bromobutane). The C3+ bromination product stream 100 may be withdrawn from the C3+ bromination reactor 95.

In the C3+ bromination reactor 95, the gaseous C3+ alkanes in the C3+ alkane stream 75 may be reacted exothermically with bromine in the third bromine stream 90, for example, at a temperature in the range of about 200° C. to about 450° C., and at a pressure in the range of about 1 atm to about 50 atm to produce gaseous alkyl bromides and HBr. In some embodiments, the temperature may be in the range of about 250° C. to about 375° C. In some embodiments, the pressure may range from about 1 atm to about 30 atm. Residence times may be, for example, from about 5 seconds to about 60 seconds and alternatively, about 15 seconds to about 45 seconds. Lower temperatures reduce the formation of soot and favor mono-bromination of propane, however at lower temperatures, longer residence times are required for complete reaction of the bromine. In some embodiments, the feeds to the C3+ bromination reactor 95 may be pre-heated to a temperature of about 250° C. to about 350° C., for example, in an inlet pre-heater zone. It should be understood that the upper limit of the operating temperature range is greater than the upper limit of the reaction initiation temperature range to which the feed mixture may be heated due to the exothermic nature of the bromination reaction. Those of ordinary skill in the art should appreciate, with the benefit of this disclosure that the bromination reaction may be a non-catalytic (thermal) or a catalytic reaction in a manner as will be evident to those of ordinary skill in the art.

It has been observed that the C3+ alkanes can also be efficiently brominated with a lesser excess of alkanes as compared to the bromination of methane so the C3+ alkane/bromine molar ratio of the feed introduced to the C3+ bromination reactor 95 may be less than about 2.5:1, in some embodiments. In some embodiments, the C3+ alkane/bromine molar ratio of the feed may be in the range of about 1.33:1 to about 2.5:1 and, preferably about 1.5:1 to about 2.0:1. By maintaining excess alkane in the C3+ bromination reactor 95 at the higher end of the range, the selectivity to mono-brominated alkanes can be increased, yet the formation of soot can be minimized even towards the low end of the range, for example. Even though more poly-brominated C3+ alkanes may be formed due to the lower excess of alkanes, the poly-brominated C3+ alkanes may not have an undesirable impact on subsequent processing steps. For example, in the reaction of the alkyl bromides over a crystalline aluminosilicate catalyst such as a zeolite catalyst to form higher molecular weight alkanes, the poly-brominated C3+ alkanes may not have excess selectively to coke formation on the catalyst because these C3+ poly-brominated alkanes still have a hydrogen-to-bromine ratio of greater than 1 and, upon dehydrohalogenation, are still able to form reactive alkyl radicals which can couple and oligomerize into higher molecular weight hydrocarbons, including aromatics, compared to the selectivity to coke formation of poly-brominated methane which have a hydrogen-to-bromine ratio of less than or equal to 1.

As illustrated, the C1 bromination product stream 50, the C2 bromination product stream 85, and the C3+ bromination product stream 100 may be combined to form combined bromination product stream 65, which may comprise alkyl bromides, such as brominated methane, brominated ethane, brominated propane, and/or brominated butane, for example. In accordance with present embodiments, the bromination product stream 65 may be routed to subsequent process units (not illustrated). In alternative embodiments (not illustrated), the C1 bromination product stream 50, the C2 bromination product stream 85, and the C3+ bromination product stream 100 may be separately routed to subsequent process units without combination. In some embodiments, the alkyl bromides present in the bromination product stream 65 may be reacted over a suitable catalyst to form higher molecular weight hydrocarbons.

Figure 3:
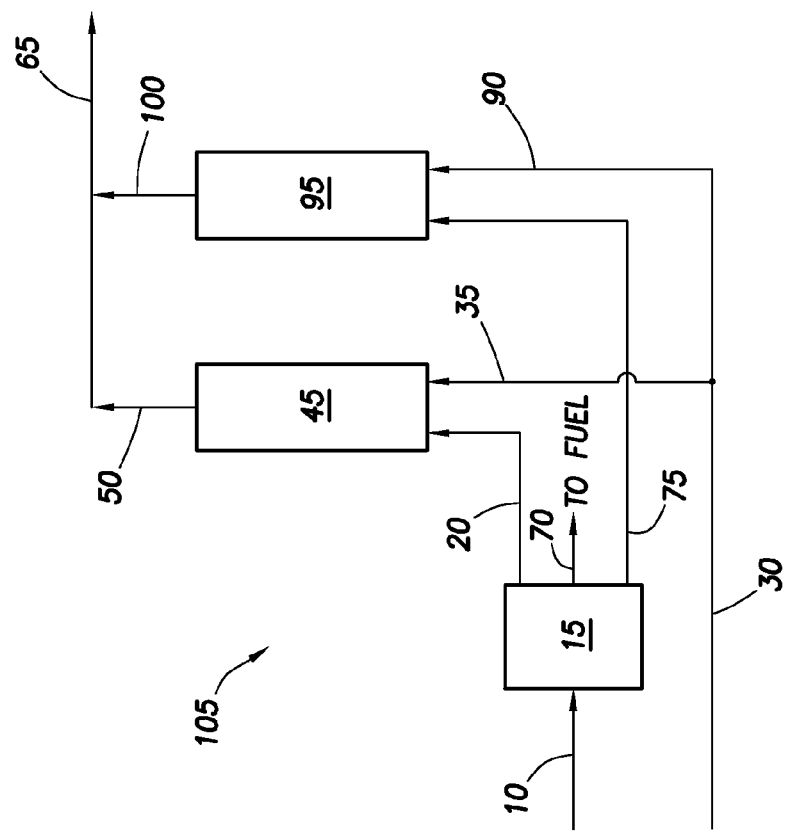
FIG. 3 is a schematic diagram illustrating a third bromination process in accordance with embodiments of the present invention.

FIG. 3 is a schematic diagram illustrating a third bromination process 105 in accordance with embodiments of the present invention. The illustrated embodiment is similar to the embodiment depicted in FIG. 2 except that the ethane stream 70 is not brominated, but rather is used for fuel for the third bromination process 105 or for subsequent process units that are not illustrated. As illustrated, the methane stream 20 may be routed to the methane bromination reactor 45, and the C3+ alkane stream 75 may be routed to the C3+ bromination reactor 95. Ethane is more difficult to brominate in the presence of more reactive higher alkanes such as propane and is also less valuable as a product, so in some embodiments it can be simpler and beneficial to utilize the ethane stream 70 as a fuel source for the process 105 rather than employ a separate reactor for ethane.

In accordance with embodiments of the present invention, the processes described above with respect to FIGS. 1-3 for the separate, parallel bromination of methane and higher alkanes may be used for the production of higher molecular weight hydrocarbons over a suitable catalyst. For example, the alkyl bromides produced as described above may be reacted over a suitable catalyst to form higher molecular weight hydrocarbons. The term "higher molecular weight hydrocarbons" as used herein refers to hydrocarbons comprising a greater number of carbon atoms than one or more components of the feedstock. For example, natural gas is typically a mixture of light hydrocarbons, predominately methane, with lesser amounts of ethane, propane, and butane, and even smaller amounts of longer chain hydrocarbons such as pentane, hexane, etc. When natural gas is used as a feedstock, higher molecular weight hydrocarbons produced in accordance with embodiments of the present invention may include a hydrocarbon comprising C2 and longer hydrocarbon chains, such as propane, butane, C5+ hydrocarbons, aromatic hydrocarbons, and mixtures thereof. In some embodiments, part or all of the higher molecular weight hydrocarbons may be used directly as a product (e.g., LPG, motor fuel, etc.). In other instances, part or all of the higher molecular weight hydrocarbons may be used as an intermediate product or as a feedstock for further processing. In yet other instances, part or all of the higher molecular weight hydrocarbons may be further processed, for example, to produce gasoline grade fuels, diesel grade fuels, and fuel additives. In some embodiments, part or all of the higher molecular weight hydrocarbons obtained by the processes of the present invention can be used directly as a motor gasoline fuel having a substantial aromatic content, as a fuel blending stock, or as feedstock for further processing such as an aromatic feed to a process producing aromatic polymers such as polystyrene or related polymers. In some cases, with some zeolite catalysts, C2 and C3 olefins are produced in the synthesis step along with ethane and propane. Such C2 and C3 olefins are potentially valuable products in some locations where petrochemical markets exist and hence can be separated and recovered for the production of polymers or other products. In other locations remote from such markets it may be advantageous to recycle these olefins back to the C3+ and/or C2+ bromination reactors. It should be noted that these C2 and C3 olefins are substantially more reactive than the respective alkane (ethane and propane) and are observed to be almost completely converted to di-bromoethylene and di-bromopropylene. Nevertheless, di-bromoethylene and di-bromopropylene are efficiently converted to higher-molecular weight products over zeolite catalysts.

The end use of the higher molecular weight hydrocarbons may depend on the particular catalyst employed in the oligomerization portion of the methods discussed below, as well as the operating parameters employed in the process. Other uses should be evident to those skilled in the art with the benefit of this disclosure.

Lower molecular weight alkanes may be used as a feedstock in the processes described herein for the production of higher molecular weight hydrocarbons. A suitable source of lower molecular weight alkanes may be natural gas. As used herein, the term "lower molecular weight alkanes" refers to methane, ethane, propane, butane, pentane or mixtures of two or more of these individual alkanes. The lower molecular weight alkanes may be from any suitable source, for example, any source of gas that provides lower molecular weight alkanes, whether naturally occurring or synthetically produced. Examples of sources of lower molecular weight alkanes for use in the processes of the present invention include, but are not limited to, natural gas, coal-bed methane, regasified liquefied natural gas, gas derived from gas hydrates and/or clathrates, gas derived from anaerobic decomposition of organic matter or biomass, gas derived in the processing of tar sands, and synthetically produced natural gas or alkanes. Combinations of these may be suitable as well in some embodiments. In some embodiments, it may be desirable to treat the feed gas to remove undesirable compounds, such as sulfur compounds and carbon dioxide. In any event, it is important to note that small amounts of carbon dioxide, e.g., less than about 2 mol %, can be tolerated in the feed gas to the processes of the present invention.

Figure 4:
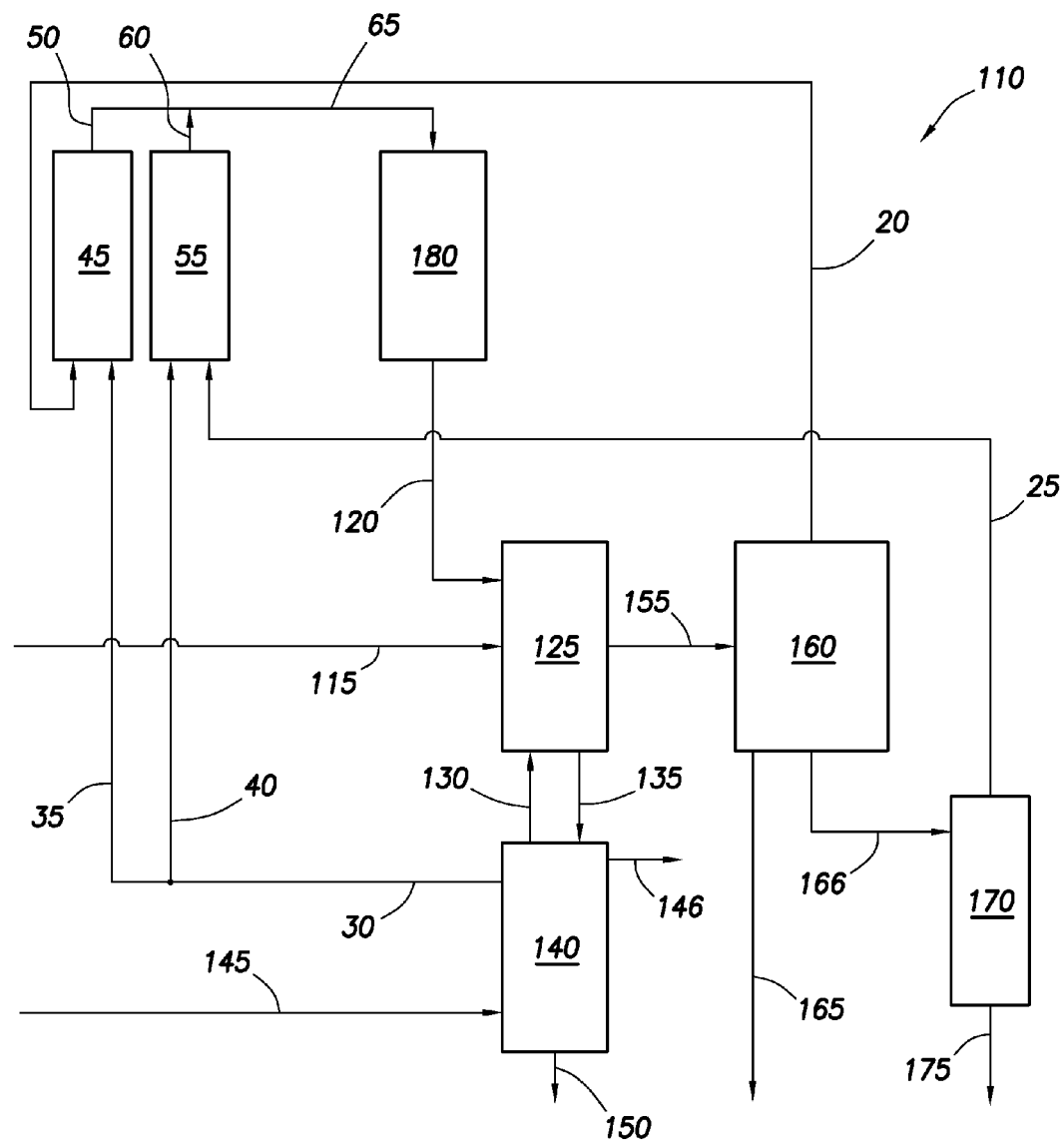
FIG. 4 is a schematic diagram illustrating an alkane-conversion process for converting lower molecular weight alkanes to higher molecular weight hydrocarbons in accordance with embodiments of the present invention.

FIG. 4 is a schematic diagram illustrating an alkane-conversion process 110 for converting lower molecular weight alkanes to higher molecular weight hydrocarbons in accordance with embodiments of the present invention. In the illustrated embodiment, a feed gas stream 115 and a synthesis reactor effluent stream 120 are fed to an HBr removal unit 125 for separation of the HBr byproduct from the hydrocarbon components in both streams. Those of ordinary skill in the art should appreciate, with the benefit of this disclosure, that the HBr is an undesired byproduct of both the bromination and synthesis reactions in the alkane-conversion process 110. In some embodiments, the feed gas stream 115 may comprise lower molecular weight alkanes, such as natural gas, for example. In some embodiments, the synthesis reactor effluent stream 120 may comprise unreacted hydrocarbons (e.g., C1-C3 hydrocarbons), higher molecular weight hydrocarbons produced by the reaction of alkyl bromides over a suitable catalyst in synthesis reactor 180, and HBr.

Any suitable technique for separation of the HBr from the hydrocarbon components may be used in accordance with embodiments of the present invention. Non-limiting examples of techniques for HBr separation include absorption of HBr into an aqueous solution, reaction of HBr with a metal oxide, or electrolysis of the HBr to form elemental bromine. In some embodiments, the HBr can be recovered from the hydrocarbon components by absorption of the HBr into stream 130 fed to the HBr removal unit 125 as should be evident to those of ordinary skill in the art with the benefit of this disclosure. Stream 130 may be, for example, an aqueous solvent (e.g., a metal bromide solution) or a non-aqueous solvent (e.g., acetic acid). As illustrated, an HBr-containing stream 135 may be withdrawn from the HBr removal unit 125 and fed to an HBr oxidation unit 140 for recovering elemental bromine that can be recycled to the bromination units (e.g., C1 bromination reactor 45, C2+ bromination reactor 55). In the HBr oxidation unit 140, the separated HBr may be oxidized with oxygen from oxygen stream 145 to produce elemental bromine and water. The oxygen stream 145 may comprise, for example, oxygen, air, or any other suitable source of oxygen. The produced water may be withdrawn via first water stream 150. The elemental bromine may be withdrawn via bromine stream 30. Oxygen-depleted gas 146 may also be withdrawn from the HBr oxidation unit 140. In the illustrated embodiment, the bromine stream 30 is divided into a first bromine stream 35 for feed to methane bromination reactor 45, and a second bromine stream 40 for feed to C2+ bromination reactor 55. While FIG. 4 illustrates absorption of the HBr into a solvent followed by regeneration of the absorption solvent and oxidation of the HBr, those of ordinary skill will appreciate that other suitable techniques, as described above may be used for deriving elemental bromine from the HBr such as via the circulation of a solid physical adsorbent such as a silica gel, etc., to preferentially adsorb the HBr from the hydrocarbon stream followed by desorption of the HBr from the solid physical adsorbent and subsequent oxidation of the HBr in unit 140. In another alternative embodiment, the circulation of a solid chemical reactant such as MgO is used to remove HBr from the hydrocarbon stream via the chemical reaction:

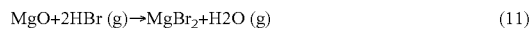

$$MgO + 2HBr\,(g) \rightarrow MgBr_2 + H2O\,(g) \qquad (11)$$

The resulting MgBr2 solid is then oxidized with an oxygen-containing gas in unit 140 according to the chemical reaction:

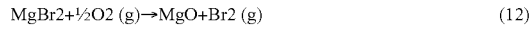

$$MgBr2 + \tfrac{1}{2}O2\,(g) \rightarrow MgO + Br2\,(g) \qquad (12)$$

In yet another embodiment, HBr could be via into a recirculated aqueous solution and subsequently converted to elemental bromine in an electrolysis cell utilizing an air-depolarized cathode contained within unit 140.

A hydrocarbon stream 155 may be withdrawn from the HBr removal unit 125 and fed to a dehydration and product recovery unit 160 wherein water may be removed from the remaining hydrocarbons via second water stream 165. Any suitable method of dehydration and product recovery may be used, including, but not limited to, solid-bed desiccant adsorption followed by refrigerated condensation, cryogenic separation, or circulating absorption oil or some other solvent. In the dehydration and product recovery unit 160, methane stream 20 may also be separated from the remaining hydrocarbons and fed to the C1 bromination reactor 45. As previously discussed, the methane stream 20 may also comprise minimal concentrations of C2+ alkanes. In the C1 bromination reactor 45, the methane stream 20 reacts with the first bromine steam 35 to form C1 bromination product stream 50 comprising alkyl bromides, HBr, and unreacted alkanes. A hydrocarbon liquid stream 166 comprising C2+ hydrocarbons may also be recovered from the dehydration and product recovery unit 160 and fed to stabilizer column 170. As illustrated, a liquid product stream 175 comprising C4+ hydrocarbons may be withdrawn from the bottom of the stabilizer column 170. C2+ alkane stream 25 may be withdrawn from the overhead of the stabilizer column 170 and fed to the C2+ bromination reactor 55. As previously discussed with respect to FIG. 1, the C2+ alkane stream may comprise ethane, propane, butane, or mixtures thereof. In the C2+ bromination reactor 55, the C2+ alkane stream 25 reacts with the second bromine stream 40 to form C2+ bromination product stream 60 comprising alkyl bromides, HBr, and unreacted alkanes.

The C1 bromination product stream 50 and the C2+ bromination product stream 60 may be combined to form bromination product stream 65 that is then fed to synthesis reactor 180, in accordance with present embodiments. In the synthesis reactor 180, the alkyl bromides in the bromination product stream 65 are reacted over a suitable catalyst in the presence of HBr to produce higher molecular weight hydrocarbons and additional HBr. Those of ordinary skill in the art should appreciate, with the benefit of this disclosure, that the particular higher molecular weight hydrocarbons produced will be dependent, for example, upon the catalyst employed in the synthesis reactor 180, the composition of the alkyl bromides introduced into the synthesis reactor 180, and the exact operating parameters employed in the synthesis reactor 180. Catalysts that may be employed in the synthesis reactor 180 include synthetic crystalline alumino-silicate catalyst, such as a zeolite catalyst, as should be recognized by those of ordinary skill in the art with the benefit of this disclosure. As discussed above, the synthesis reactor effluent stream 120 may be withdrawn from the synthesis reactor 180 and fed to the HBr removal unit 125.

Figure 5:
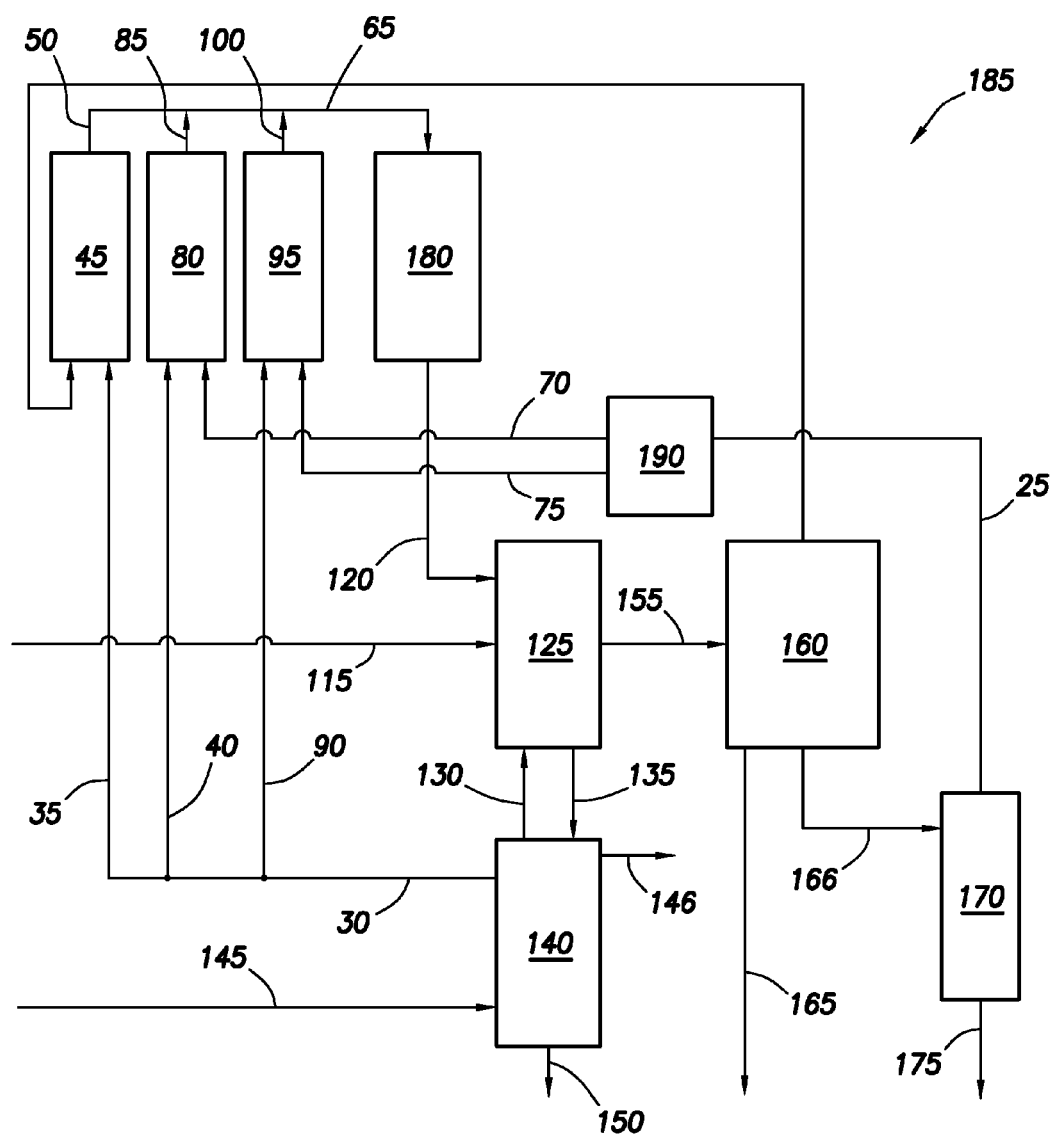
FIG. 5 is a schematic diagram illustrating a second alkane-conversion process for converting lower molecular weight alkanes to higher molecular weight hydrocarbons in accordance with embodiments of the present invention.

FIG. 5 is a schematic diagram illustrating a second alkane-conversion process 185 for converting lower molecular weight alkanes to higher molecular weight hydrocarbons in accordance with embodiments of the present invention. The illustrated embodiment is similar to the alkane-conversion process 110 depicted in FIG. 4 except that the process 185 includes separate, parallel C2 bromination and C3+ bromination reactors 80, 95 with the bromine stream 30 being split into a first bromine stream 35, a second bromine stream 40, and a third bromine stream 90 for feeding the C1 bromination reactor 45, C2 bromination reactor 80, and C3+ bromination reactor 95, respectively. As illustrated, the C2+ alkane stream 25 may be withdrawn from the overhead of the stabilizer column 170 and fed to fractionation column 190 for separation of the C2+ alkane stream 25 into an ethane stream 70 and a C3+ alkane stream 75. While fractionation column 190 is illustrated for separation of the ethane from the heavier hydrocarbons, other suitable techniques for hydrocarbon separation may be used as should be evident to those of ordinary skill in the art with the benefit of this disclosure. The ethane stream 70 may be routed to the C2 bromination reactor 80 for reaction with the second bromine stream 40, and the C3+ alkane stream may be routed to the C3+ bromination reactor 95 for reaction with the third bromine stream 90. In the illustrated embodiment, the C1 bromination product stream 50, C2 bromination product stream 85, and C3+ bromination product stream 100 may be withdrawn from the separate, parallel C1 bromination, C2 bromination, and C3+ bromination reactors 45, 80, 95.

Figure 6:
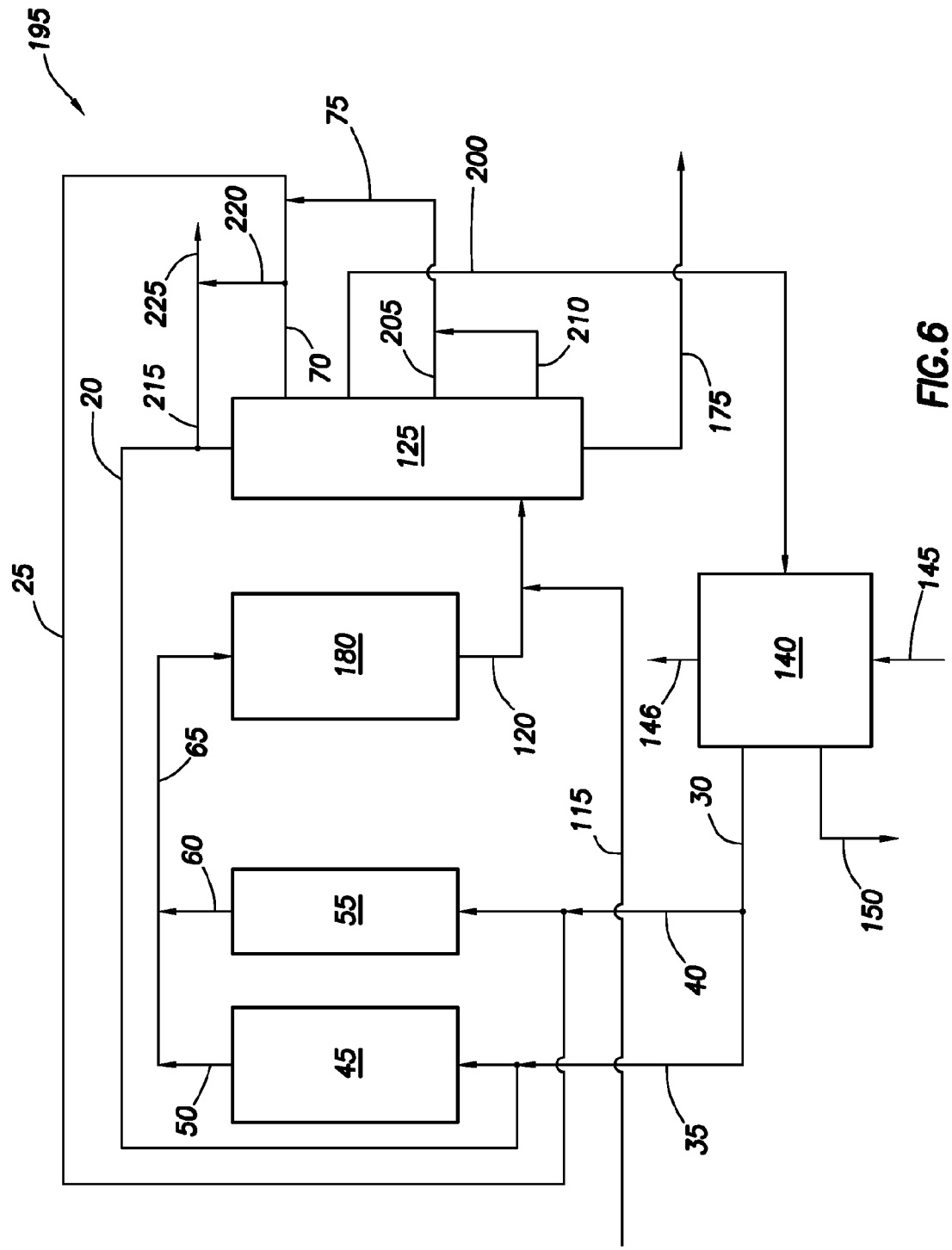
FIG. 6 is a schematic diagram illustrating a third alkane-conversion process in accordance with embodiments of the present invention.

FIG. 6 is a schematic diagram illustrating a third alkane-conversion process 195 in accordance with embodiments of the present invention. The illustrated embodiment is similar to the alkane-conversion process 110 depicted in FIG. 4 except that the process 195 does not include a separate dehydration and product recovery unit 160 for separation of the hydrocarbon components into their respective fractions for product recovery and recycle. Instead, the feed gas stream 115 and synthesis reactor effluent 120 are fed to the HBr removal unit 125 wherein the combined feeds are separated to form, for example, a methane stream 20, an ethane stream 70, an HBr stream 200, a propane stream 205, a butane stream 210, and a liquid product stream 175. Any suitable technique or combination of techniques may be used for separation of the HBr and hydrocarbons in the HBr removal unit 125, including, for example, cryogenic separation, fractionation, extractive distillation, or a refrigerated lean-oil process, among others, as should be evident to those of ordinary skill in the art with the benefit of this disclosure. The methane stream 20 comprising primarily methane and small quantities of heavier hydrocarbons can be withdrawn from the HBr removal unit 125 and fed to the C1 bromination reactor 45. In the illustrated embodiment, a C1 fuel stream 215 may be split from the methane stream 20 and used, for example, as fuel for the process 195. In the illustrated embodiment, the ethane stream 70, propane stream 205, and butane stream 210 may be combined to form C2+ alkane stream 25 and then fed to the C2+ bromination reactor 55. In the illustrated embodiment, a C2 fuel stream 220 may be split from the ethane stream 70 and used, for example, as fuel for the process. In some embodiments, the C1 fuel stream 215 and C2 fuel stream 220 may be combined to form a recovered fuel stream 225. HBr stream 200 withdrawn from the HBr removal unit 125 can be fed to the HBr oxidation unit 140 for recovery of elemental bromine. Liquid product stream 175 comprising C4+ hydrocarbons may also be withdrawn from the HBr recovery unit 125.

Figure 7:
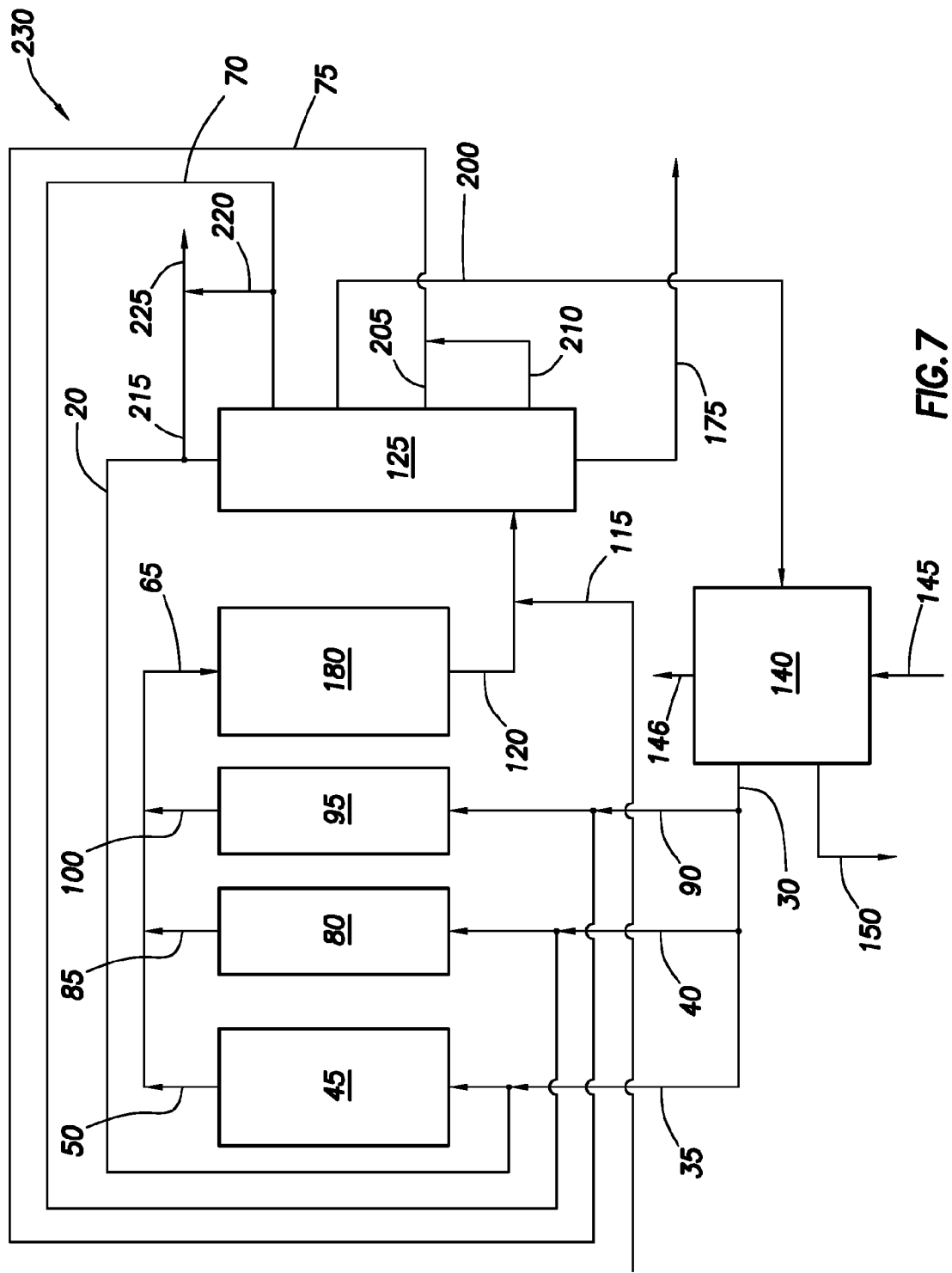
FIG. 7 is a schematic diagram illustrating a fourth alkane-conversion process in accordance with embodiments of the present invention.

FIG. 7 is a schematic diagram illustrating a fourth alkane-conversion process 230 in accordance with embodiments of the present invention. The illustrated embodiment is similar to the third alkane-conversion process 195 depicted in FIG. 6 except that the process 230 includes separate, parallel C2 bromination and C3+ bromination reactors 80, 95 with the bromine stream 30 being split into a first bromine stream 35, a second bromine stream 40, and a third bromine stream 90 for feeding the C1 bromination reactor 45, C2 bromination reactor 80, and C3+ bromination reactor 95, respectively. As illustrated, the methane stream 20 may be withdrawn from the HBr removal unit 125 and fed to the C1 bromination reactor 45 for reaction with the first bromine stream 35. The ethane stream 70 may be withdrawn from the HBr removal unit 125 and fed to the C2 bromination reactor 80 for reaction with the second bromine stream 40. In the illustrated embodiment, the propane stream 205 and butane stream 210 may be withdrawn from the HBr removal unit 125, combined to form C3+ alkane stream 75, and then fed to the C3+ bromination reactor 95 for reaction with the third bromine stream 90.

To facilitate a better understanding of the present invention, the following examples of certain aspects of some embodiments are given. The following examples should not be read or construed in any manner to limit, or define, the entire scope of the invention.

EXAMPLE 1

Figure 8:
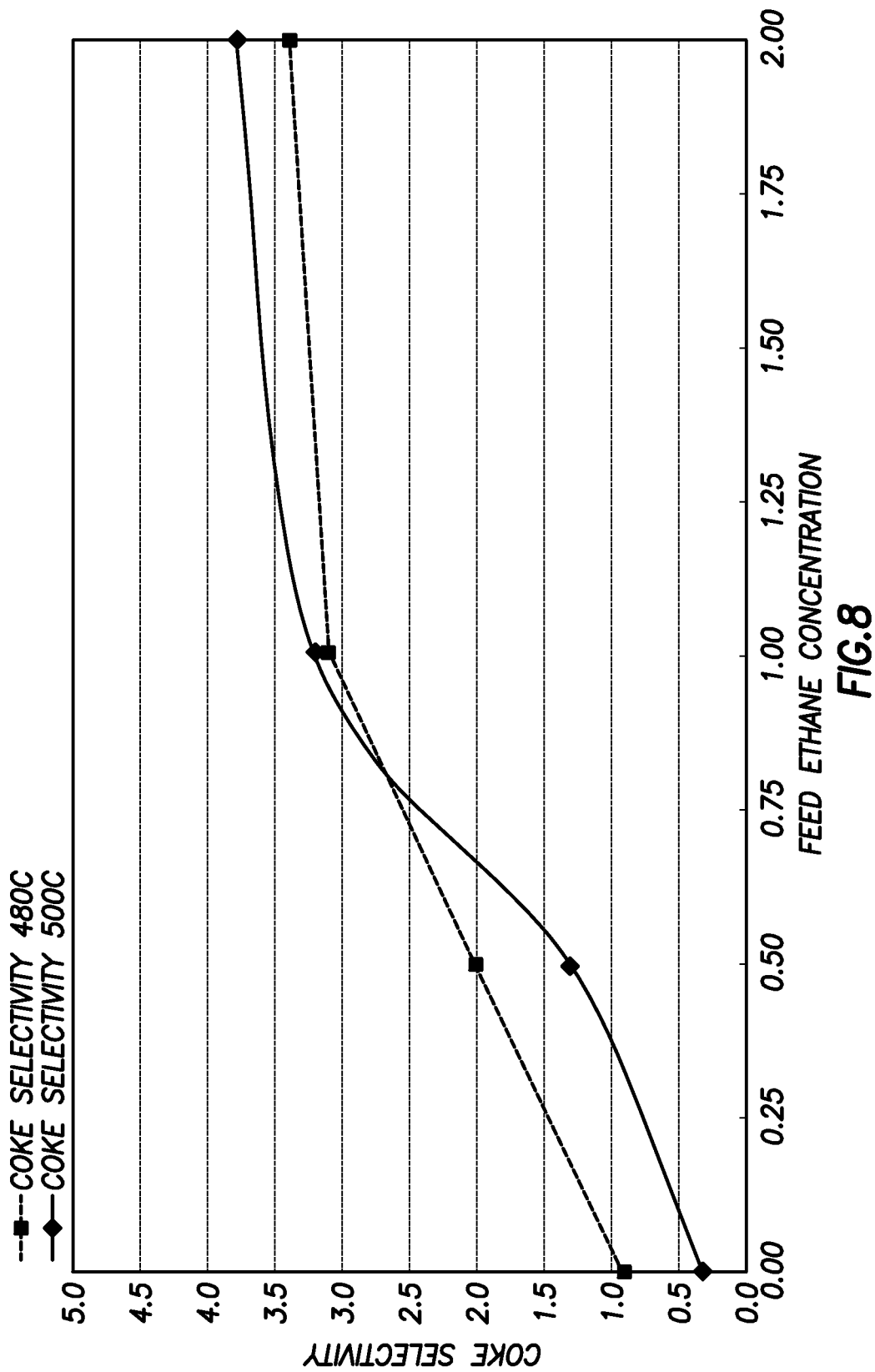
FIG. 8 is a plot of coke selectivity versus feed ethane concentration for an example bromination process.
Figure 9:
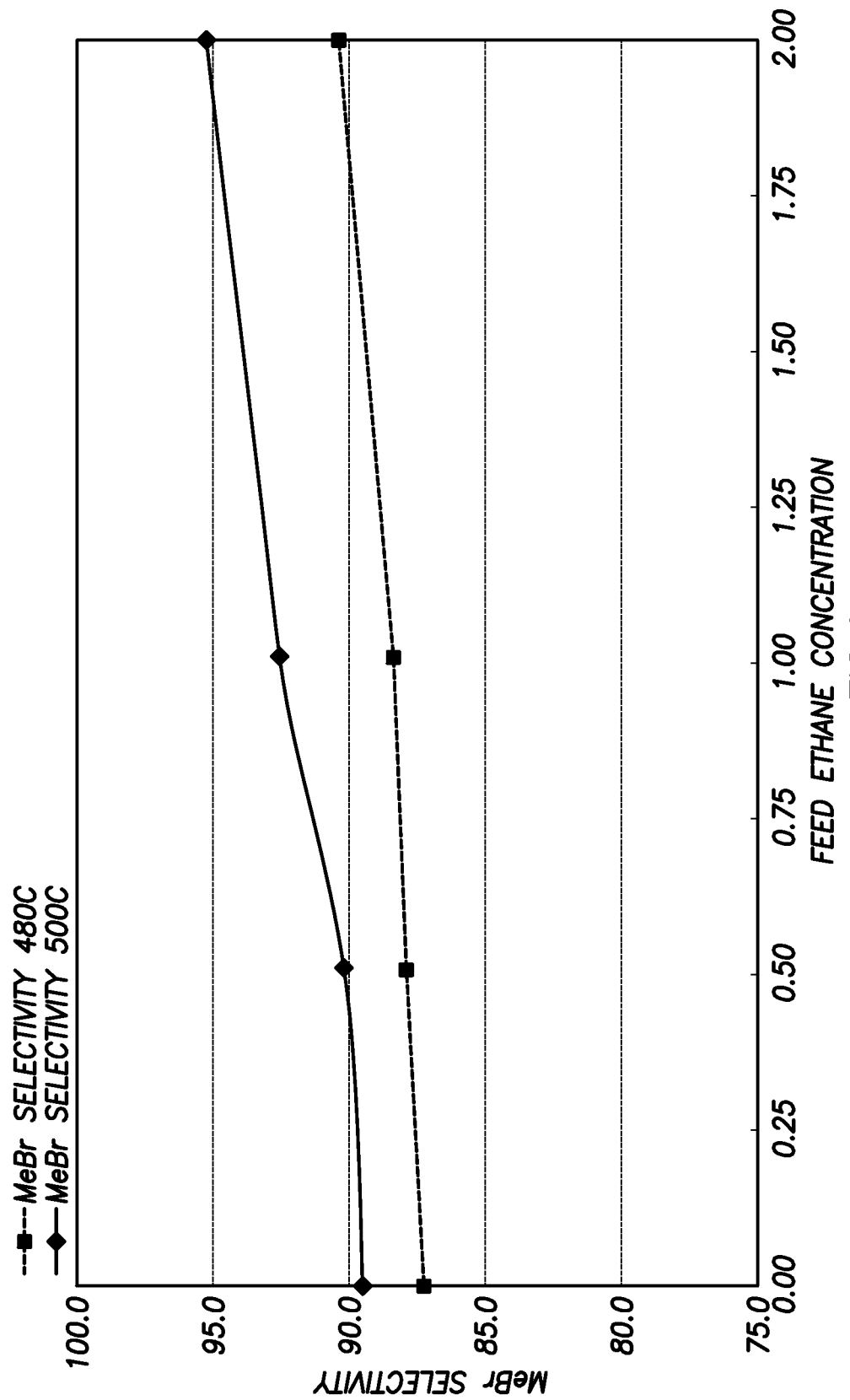
FIG. 9 is a plot of mono-bromomethane selectivity versus feed ethane concentration for an example bromination process.

Various mixtures of methane and ethane are reacted in an open-tube reactor with bromine at reactor skin temperatures of 480° C. and 500° C. and a methane-to-bromine mole ratio of 3:1. The concentration of ethane in the methane varies from 0.0 mol % to 2 mol %. The residence time is about 33 seconds. The reactor is constructed of ⅜-inch outside diameter Iconel alloy tubing (0.035-inch wall thickness) and is 84 inches in length. The soot formed in the reactor is estimated from carbon dioxide and carbon monoxide generated during reactor regeneration. The coke selectivity is calculated as the ratio of coke formed to the sum of mono-bromomethane and di-bromomethane in the reactor effluent and twice the feed ethane concentration. FIG. 8 is a plot of coke selectivity versus feed ethane concentration. As illustrated by FIG. 8, the coke selectivity increases with increases in feed ethane concentration. It should be noted that, at an ethane feed concentration of less than 1 mol %, a higher coke selectivity is unexpectedly shown at 480° C. than 500° C. This result could be due to a number of different factors, including expected scatter data due to low range of coke formation (0 to 4%) and small temperature differential (20° C.). FIG. 9 is a plot of mono-bromomethane selectivity versus feed ethane concentration. As illustrated by FIG. 9, the mono-bromomethane selectivity at 500° C. improves from 90% with no ethane in the feed to near 95% with an ethane concentration of 2 mol %. Similar trends are shown at 480° C.

EXAMPLE 2

Figure 10:
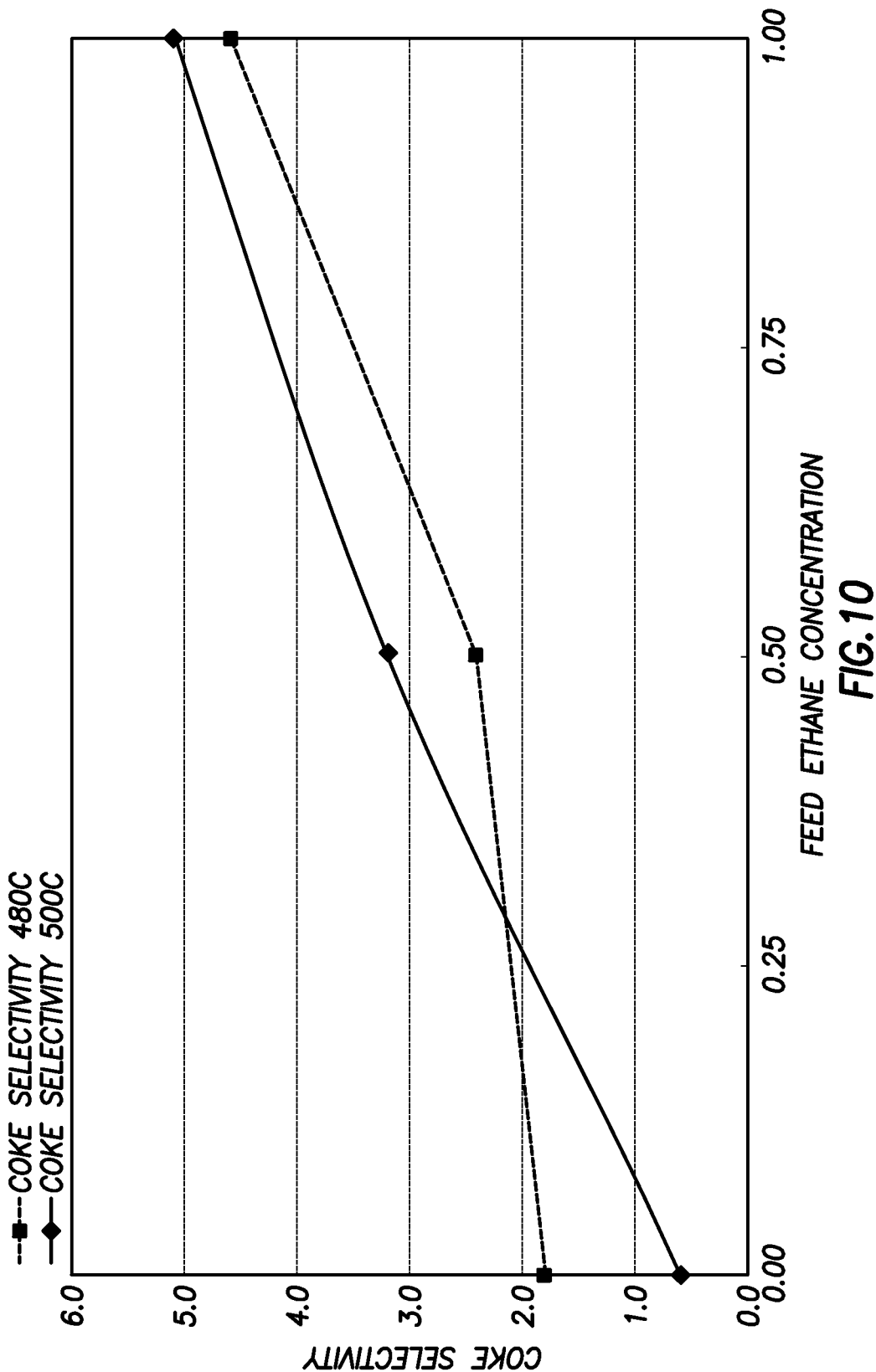
FIG. 10 is a plot of coke selectivity versus feed ethane concentration for an example bromination process.
Figure 11:
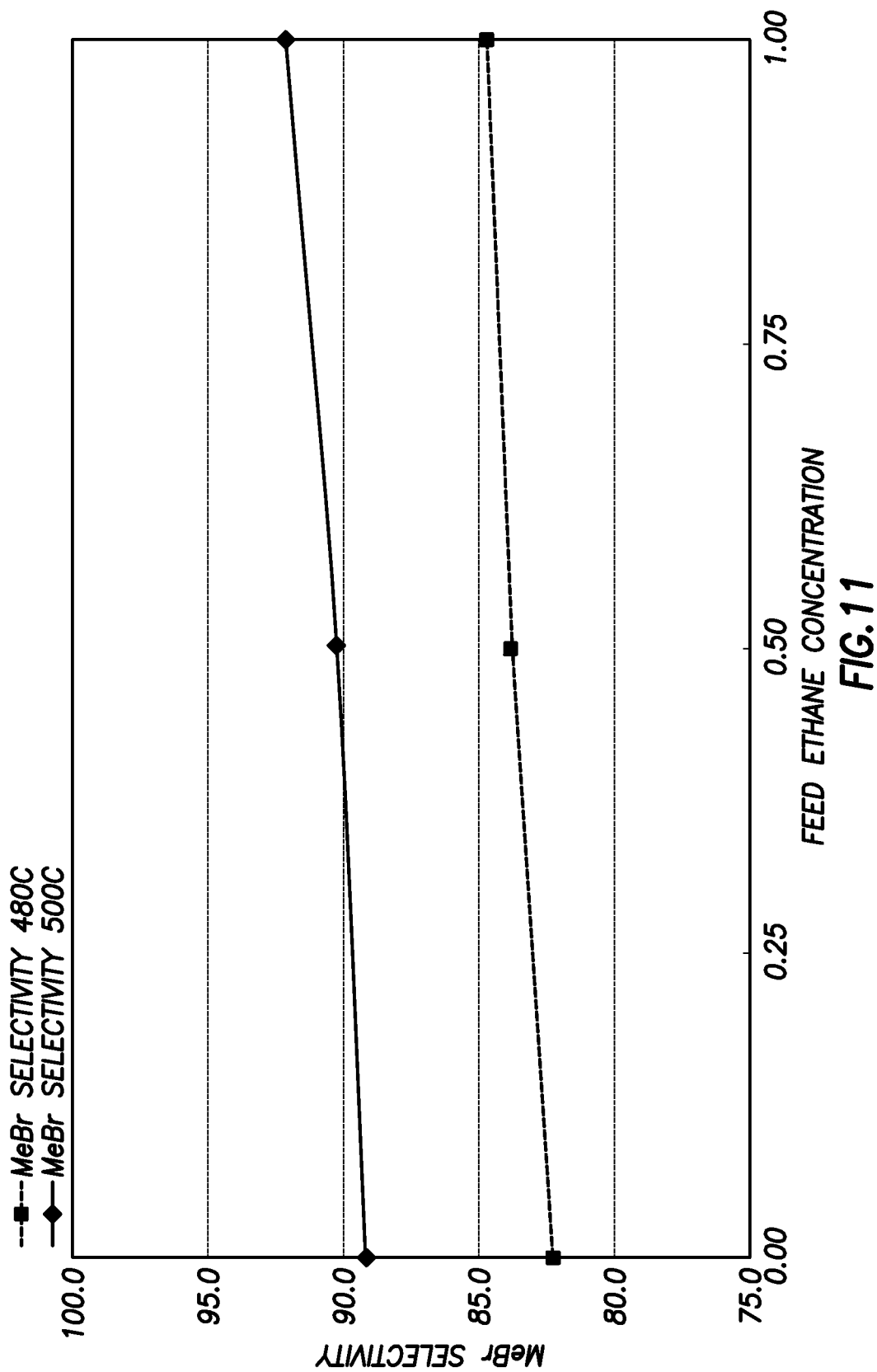
FIG. 11 is a plot of mono-bromomethane selectivity versus feed ethane concentration for an example bromination process.

Various mixtures of methane and ethane are reacted in a reactor with bromine at reactor skin temperatures of 480° C. and 500° C. and a methane-to-bromine mole ratio of 3:1. The concentration of ethane in the methane varies from 0.0 mol % to 2 mol %. The reactor is filled with ¼-inch rashig rings. The residence time is about 27 seconds. The reactor is constructed of ⅜-inch outside diameter Iconel alloy tubing (0.035-inch wall thickness) and is 84 inches in length. The coke selectivity is calculated as described above for Example 1. FIG. 10 is a plot of coke selectivity versus feed ethane concentration. As illustrated by FIG. 10, the coke selectivity increases with increases in feed ethane concentration. The coke selectivity is higher for the packed reactor in this example than for the open-tube reactor of Example 1. FIG. 11 is a plot of mono-bromomethane selectivity versus feed ethane concentration. As illustrated by FIG. 11, the mono-bromomethane selectivity improves at both 480° C. and 500° C. with increasing feed ethane concentration.

EXAMPLE 3

Propane is reacted with bromine in an empty tube at a temperature of 325° C., a molar feed ratio of propane to bromine of about 2:1, and volumetric residence times of 30 seconds and 60 seconds. Volumetric residence time is defined as the ratio of reactor volume to the inlet gas volumetric flow rate at the process temperature and pressure. The results are shown below. As illustrated, a monobromide selectivity of close to 90% is achieved. The coke formation is below detection limit.

TABLE 1

| Temperature | 325° C. | 325° C. |
|---|---|---|
| Residence Time | 30 s | 60 s |
| Feed | | |
| $C_3H_8$—$Br_2$ Molar Ratio | 2 | 2 |
| Product Selectivity (mol %) | | |
| $C_3Br$ | 89% | 91% |
| $C_3Br_2$ | 10% | 7% |
| Other RBr | 1% | 2% |
| % Conversion | | |
| $C_3$ | 47% | 47% |
| C Balance | 94% | 91% |
| Coke | 0% | 0% |

EXAMPLE 4

A mixture of propane and butane is reacted in an empty tube with bromine at a temperature of 325° C., a molar feed ratio of alkane to bromine of about 2.5:1, and a volumetric residence time of 60 seconds. The results are shown below. The bromopropane/di-bromopropane ratio is high, however, the bromobutane/di-bromobutane ratio is not high. The butane conversion (65%) is higher than that for propane (23%), since butane bromination is favored over propane bromination at this temperature. The coke formation is below detection limit. Small amounts of 2,3-dibromo-1-propene and 1,2,3-tribromopropane were also detected in this test.

TABLE 2

| Temperature | 325° C. |
|---|---|
| Residence Time | 60 s |
| Feed | |
| Alkane-$Br_2$ Molar Ratio | 2.5 |
| $C_3$ (mol %) | 84% |
| $C_4$ (mol %) | 16% |
| Product Selectivity (mol %) | |
| $C_3Br$ | 51% |
| $C_3Br_2$ | 3% |
| $C_4Br$ | 28% |
| $C_4Br_2$ | 17% |
| $C_4Br_3$ | 1% |
| Other RBr | <1% |
| Conversion | |
| $C_3$ | 23% |
| $C_4$ | 65% |
| C Balance | 93% |
| Coke | 0% |

EXAMPLE 5

A mixture of gaseous light hydrocarbons is reacted with bromine in an empty tube at temperatures of 300° C. and 375°, a molar feed ratio of hydrocarbon to bromine of about 2.1:1, and volumetric residence times of 30 seconds and 60 seconds. The molar feed ratio of hydrocarbon to bromine is slightly reduced to about 2.0:1 for third run and more significantly reduced to about 1.33:1 for the fourth run. The gaseous light hydrocarbons fed to the tube include 1.7 mol % ethylene, 7.3 mol % ethane, 0.9 mol % propylene, 76 mol % propane, and 13.9 mol % butane. The results are shown below. The results indicate that propane conversion increases with temperature. The results further indicate that decreasing the alkane-to-bromine ratio (increasing the bromine/lights ratio) increases the propane and butane conversion. There is no significant change in ethane conversion with this ratio change since the ethane fraction in the feed is low, and the reactivity is in the following order: butane>propane>ethane. The ethane conversion is low in the presence of propane and ethane due to its relatively lower reactivity. Ethylene and propylene in the feed react with bromine to produce di-bromoethane and di-bromopropane, respectively.

TABLE 3

| Temperature | 300° C. | 375° C. | 375° C. | 375° C. |
|---|---|---|---|---|
| Residence Time | 60 s | 60 s | 60 s | 60 s |
| Feed | | | | |
| Alkane-$Br_2$ Molar Ratio | 2.1 | 2.1 | 2.0 | 1.33 |
| $C_2H_4$ (mol %) | 1.7% | 1.7% | 1.7% | 1.7% |
| $C_2H_6$ (mol %) | 7.3% | 7.3% | 7.3% | 7.3% |
| $C_3H_6$ (mol %) | 0.9% | 0.9% | 0.9% | 0.9% |
| $C_3H_8$ (mol %) | 76% | 76% | 76% | 76% |
| i-$C_4H_{10}$ (mol %) | 13.9% | 13.9% | 13.9% | 13.9% |
| Product Selectivity (mol %) | | | | |
| $C_2Br$ | 1% | 1% | 1% | 1% |
| $C_2Br_2$ | 4% | 3% | 3% | 2% |
| $C_2Br_3$ | <1% | <1% | <1% | <1% |
| $C_2Br_4$ | <1% | <1% | <1% | <1% |
| $C_3Br$ | 52% | 49% | 47% | 60% |
| $C_3Br_2$ | 7% | 3% | 6% | 8% |
| $C_4Br$ | 12% | 18% | 17% | 7% |

TABLE 3-continued

| | | | | |
|---|---|---|---|---|
| $C_4Br_2$ | 17% | 24% | 23% | 19% |
| $C_4Br_3$ | 6% | 1% | <1% | <1% |
| Other RBr | <1% | <1% | 2% | 2% |
| % Conversion | | | | |
| $C_2H_4$ | 100% | 100% | 100% | 96% |
| $C_2H_6$ | 16% | 11% | 11% | 8% |
| $C_3H_6$ | 5% | 0% | 0% | 0% |
| $C_3H_8$ | 25% | 31% | 31% | 44% |
| $i\text{-}C_4H_{10}$ | 70% | 72% | 77% | 89% |
| C Balance | 92% | 90% | 90% | 92% |
| Coke | 0% | 0% | 0% | 0% |

EXAMPLE 6

A mixture of gaseous light hydrocarbons is reacted with bromine in an empty tube at a temperature of 325° C., a molar feed ratio of hydrocarbons to bromine of about 1.33:1, and a volumetric residence time of 60 seconds. The gaseous light hydrocarbons fed to the tube include 78 mol % ethane, 19 mol % propane, and 1 mol % butane. The results are shown below. The results indicate that ethane conversion is increased as compared to Example 5 due the increased fraction of ethane in the feed and that the propane and butane conversion is high.

TABLE 4

| | |
|---|---|
| Temperature | 325° C. |
| Residence Time | 60 s |
| Feed | |
| Alkane-$Br_2$ Molar Ratio | 1.33 |
| $C_2H_6$ (mol %) | 78% |
| $C_3H_6$ (mol %) | 19% |
| $C_4H_{10}$ (mol %) | 1% |
| Product Selectivity (mol %) | |
| $C_2Br$ | 42% |
| $C_2Br_2$ | 10% |
| $C_2Br_3$ | <1% |
| $C_2Br_4$ | <1% |
| $C_3Br$ | 12% |
| $C_3Br_2$ | 33% |
| $C_4Br$ | <1% |
| $C_4Br_2$ | <1% |
| $C_4Br_3$ | <1% |
| Other RBr | 1% |
| % Conversion | |
| $C_2H_6$ | 46% |
| $C_3H_8$ | 99% |
| $C_4H_{10}$ | 96% |
| C Balance | 83.8% |
| Coke | 0% |

Certain embodiments of the methods of the invention are described herein. Although major aspects of what is to believed to be the primary chemical reactions involved in the methods are discussed in detail as it is believed that they occur, it should be understood that side reactions may take place. One should not assume that the failure to discuss any particular side reaction herein means that that reaction does not occur. Conversely, those that are discussed should not be considered exhaustive or limiting. Additionally, although figures are provided that schematically show certain aspects of the methods of the present invention, these figures should not be viewed as limiting on any particular method of the invention.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. All numbers and ranges disclosed above may vary by some amount. Whenever a numerical range with a lower limit and an upper limit is disclosed, any number and any included range falling within the range are specifically disclosed.

What is claimed is:

1. A bromine-based process for converting alkanes to liquid hydrocarbons that includes alkane bromination, the process comprising:
   brominating a methane stream comprising methane and having less than about 2 mol % of ethane to form methane bromination products comprising brominated methane and a first fraction of hydrogen bromide;
   separately brominating a C2+ alkane stream comprising an alkane having 2 or more carbon atoms to form C2+ methane bromination products comprising brominated alkanes having 2 or more carbon atoms and a second fraction of hydrogen bromide; and
   combining and catalytically reacting at least a portion of the brominated methane and the brominated alkanes to form higher molecular hydrocarbons.

2. The process of claim 1 wherein the step of brominating the methane stream occurs at a temperature of greater than about 400° C.

3. The process of claim 1 wherein the step of separately brominating the C2+ alkane stream occurs at a temperature in a range of about 250° C. to about 450° C.

4. The process of claim 1 wherein the step of brominating the methane stream occurs at a temperature in a range of from about 490° C. to about 570° C., and wherein the step of separately brominating the C2+ alkane stream occurs at a temperature in a range of about 250° C. to about 375° C.

5. The process of claim 1 wherein bromination of the methane stream results in selectivity to mono-bromomethane for the brominated C1 alkanes of at least about 90 mol %.

6. The process of claim 1 wherein the methane-to-bromine ratio in the step of brominating the methane stream is at least about 2.5:1, and wherein the C2+ alkane-to-bromine ratio in the step of brominating the C2+ alkane stream is in a range of about 1.33:1 to about 2.5:1.

7. The process of claim 1 wherein the step of separately brominating a C2+ alkane stream comprises:
   separately brominating an ethane stream comprising ethane to form an ethane bromination stream comprising brominated ethane and a third fraction of hydrogen bromine; and
   separately brominating a C3+ alkane stream comprising propane and butane to form the C2+ methane bromination product stream, the brominated alkanes having 2 or more carbon atoms comprising brominated propane and brominated butane.

8. The process of claim 7 wherein the ethane stream comprises alkanes having 3 or more carbon atoms in an amount of less than about 1 mol %.

9. The process of claim 7 wherein residence times in a methane bromination reactor for the step of brominating the methane stream are in a range of from about 15 seconds to about 60 seconds, residence times in an ethane bromination reactor for the step of brominating the ethane stream are in a range of from about 15 seconds to about 45 seconds, and residence times in a C3+ bromination reactor the step of brominating the C3+ alkane stream are in a range of from about 15 seconds to about 45 seconds.

10. The process of claim 1 wherein the C2+ alkane stream comprises propane and butane, and wherein ethane is separated from the methane stream and C2+ alkane stream for use as a fuel.

11. The process of claim 1 wherein the higher molecular weight hydrocarbons comprise hydrocarbons having 5 or more carbon atoms.

12. The process of claim 1 comprising deriving elemental bromine from the first, second, and third fractions of hydrogen bromide, wherein the elemental bromine is recycled for use in the step of brominating the methane stream and brominating the C2+ alkane stream.

13. The process of claim 1 wherein the step of deriving elemental bromine comprises adsorbing the first, second, and third fractions of hydrogen bromide into an aqueous stream and oxidizing the resulting stream to form the elemental bromine.

14. The process of claim 1 further comprising separating the C2+ alkane stream from a stream comprising the higher molecular hydrocarbons.

15. A bromine-based process for converting alkanes to liquid hydrocarbons that includes alkane bromination, the process comprising:
    brominating a methane stream in a bromination reactor to form methane bromination products comprising brominated methane and a first fraction of hydrogen bromide, the methane stream comprising methane and having less than about 1 mol % of ethane and less than about 0.10 mol % of hydrocarbons having 3 or more carbon atoms;
    separately brominating a C2+ alkane stream in a C2+ bromination reactor to form C2+ methane bromination products comprising brominated alkanes having 2 or more carbon atoms and a second fraction of hydrogen bromide, the C2+ alkane stream comprising ethane, propane, and butane; and
    combining and catalytically reacting at least a portion of the brominated methane and the brominated alkanes in a synthesis reactor to form higher molecular weight hydrocarbons and a third fraction of hydrogen bromide.

16. The process of claim 15 further comprising:
    feeding a feed gas stream and an effluent stream from the synthesis reactor into an HBr removal unit, the feed gas stream comprising lower molecular weight hydrocarbons, the effluent stream comprising the higher molecular weight hydrocarbons and the first, second, and third fractions of hydrogen bromide;
    recovering methane from the HBr removal unit and recycling at least a portion of the methane to the bromination reactor via the methane stream;
    recovering ethane and propane from the HBr removal unit and recycling at least a portion of the ethane and propane to the C2+ bromination reactor via the C2+ bromination stream;
    recovering a liquid product stream from the HBr removal unit, the liquid product stream comprising hydrocarbons having 4 or more carbon atoms; and
    recovering an HBr stream from the HBr removal unit, the HBr stream comprising the first, second, and third fractions of hydrogen bromide.

17. The process of claim 16 further comprising oxidizing the HBr stream to form elemental bromine and recycling the elemental bromine to the bromination reactor and the C2+ bromination reactor.

18. The process of claim 15 wherein the step of brominating the methane stream occurs at a temperature in a range of from about 490° C. to about 570° C., wherein the step of separately brominating the C2+ alkane stream occurs at a temperature in a range of about 250° C. to about 375° C., wherein bromination of the methane stream results in selectivity to mono-bromomethane for the brominated alkanes of at least about 90 mol %, wherein the methane-to-bromine ratio in the step of brominating the methane stream is at least about 2.5:1, and wherein the C2+ alkane-to-bromine ratio in the step of brominating the C2+ alkane stream is in a range of about 1.33:1 to about 2.5:1.

19. The method of claim 1 further comprising processing the higher molecular weight hydrocarbons to at least one product selected from the group consisting of a gasoline grade fuel, a diesel grade fuel, and a fuel additive.

20. The method of claim 1 wherein the higher molecular weight hydrocarbons comprise C2 and C3 olefins.

\* \* \* \* \*